(12) United States Patent
Gunay et al.

(10) Patent No.: US 9,068,957 B2
(45) Date of Patent: Jun. 30, 2015

(54) EVALUATING HEPARIN PREPARATIONS

(75) Inventors: Nur Sibel Gunay, Chestnut Hill, MA (US); Miroslaw Lech, North Chelmsford, MA (US); Sucharita Roy, Tyngsboro, MA (US); John Schaeck, Somerville, MA (US); Jennifer Ozug, Norwood, MA (US); Daniela Beccati, Watertown, MA (US); Ishan Capila, Ashland, MA (US)

(73) Assignee: MOMENTA PHARMACEUTICALS, INC., Cambridge, MA (US)

( * ) Notice: Subject to any disclaimer, the term of this patent is extended or adjusted under 35 U.S.C. 154(b) by 176 days.

(21) Appl. No.: 14/000,559

(22) PCT Filed: Feb. 21, 2012

(86) PCT No.: PCT/US2012/025920
§ 371 (c)(1),
(2), (4) Date: Jan. 6, 2014

(87) PCT Pub. No.: WO2012/115952
PCT Pub. Date: Aug. 30, 2012

(65) Prior Publication Data
US 2014/0114056 A1     Apr. 24, 2014

Related U.S. Application Data

(60) Provisional application No. 61/559,228, filed on Nov. 14, 2011, provisional application No. 61/444,985, filed on Feb. 21, 2011.

(51) Int. Cl.
G01N 33/15      (2006.01)
C08B 37/00      (2006.01)
C08L 5/10       (2006.01)

(52) U.S. Cl.
CPC ............ *G01N 33/15* (2013.01); *C08B 37/0075* (2013.01); *C08L 5/10* (2013.01)

(58) Field of Classification Search
CPC ........................ G01N 33/15; C08B 37/0075
USPC ............................................ 536/21; 73/61.41
See application file for complete search history.

(56) References Cited

U.S. PATENT DOCUMENTS

| | | |
|---|---|---|
| 3,832,253 A | 8/1974 | DiPalma |
| 3,854,480 A | 12/1974 | Zaffaroni |
| 4,452,775 A | 6/1984 | Kent |
| 4,652,555 A | 3/1987 | Goulay et al. |
| 4,667,014 A | 5/1987 | Nestor, Jr. et al. |
| 4,686,288 A | 8/1987 | Lormeau et al. |
| 4,687,765 A | 8/1987 | Vairel et al. |
| 4,692,435 A | 9/1987 | Lormeau et al. |
| 4,748,034 A | 5/1988 | de Rham |
| 4,791,195 A | 12/1988 | Bianchini et al. |
| 4,826,827 A | 5/1989 | Lormeau et al. |
| 4,847,338 A | 7/1989 | Linhardt et al. |
| 4,916,219 A | 4/1990 | Linhardt et al. |
| 4,933,326 A | 6/1990 | Bianchini et al. |
| 4,977,250 A | 12/1990 | Diaz et al. |
| 4,981,955 A | 1/1991 | Lopez |
| 4,990,502 A | 2/1991 | Lormeau et al. |
| 5,010,063 A | 4/1991 | Piani et al. |
| 5,013,724 A | 5/1991 | Petitou et al. |
| 5,013,725 A | 5/1991 | Isomura et al. |
| 5,019,649 A | 5/1991 | Lormeau et al. |
| 5,032,679 A | 7/1991 | Brandley et al. |
| 5,039,529 A | 8/1991 | Bergendal et al. |
| 5,084,564 A | 1/1992 | Vila et al. |
| 5,104,860 A | 4/1992 | Piani et al. |
| 5,106,734 A | 4/1992 | Nielsen |
| 5,110,918 A | 5/1992 | Casu et al. |
| 5,164,378 A | 11/1992 | Conti et al. |
| 5,239,660 A | 8/1993 | Ooi |
| 5,264,425 A | 11/1993 | Dal Pozzo et al. |
| 5,296,471 A | 3/1994 | Holme et al. |
| 5,340,932 A | 8/1994 | Fussi et al. |
| 5,380,716 A | 1/1995 | Conrad et al. |
| 5,389,618 A | 2/1995 | Debrie |
| 5,403,827 A | 4/1995 | De-Ambrosi |
| 5,410,039 A | 4/1995 | Ungarelli et al. |
| 5,430,132 A | 7/1995 | Silvano et al. |
| 5,430,133 A | 7/1995 | Piani et al. |
| 5,599,801 A | 2/1997 | Branellec et al. |
| 5,668,118 A | 9/1997 | Kennedy |
| 5,696,100 A | 12/1997 | Holme et al. |

(Continued)

FOREIGN PATENT DOCUMENTS

| | | |
|---|---|---|
| EP | 121067 B1 | 10/1984 |
| EP | 244235 B1 | 11/1987 |
| EP | 244236 A2 | 11/1987 |
| EP | 245813 B1 | 11/1987 |
| EP | 268885 B1 | 6/1988 |
| EP | 293539 A2 | 12/1988 |
| EP | 302034 B1 | 2/1989 |
| EP | 319559 A1 | 6/1989 |
| EP | 347588 B1 | 12/1989 |
| EP | 423151 B1 | 9/1993 |

(Continued)

OTHER PUBLICATIONS

Keiser et al., "Preimplantation screening for transgenesis using an embryonic specific promoter and green fluorescent protein", Cloning, 2001, vol. 3, No. 1, pp. 21-30.

(Continued)

*Primary Examiner* — Brandon Fetterolf
*Assistant Examiner* — Yih-Horng Shiao
(74) *Attorney, Agent, or Firm* — Lando & Anastasi LLP

(57) ABSTRACT

Methods of evaluating heparin preparations, e.g., for suitability for use as a drug or for use in making a drug, by determining the absence, presence or amount of a structural signature, wherein, e.g., the structural signature is indicative of the methods used to make the heparin preparation.

21 Claims, 3 Drawing Sheets

(56) References Cited

U.S. PATENT DOCUMENTS

| | | |
|---|---|---|
| 5,707,973 A | 1/1998 | Baron et al. |
| 5,707,974 A | 1/1998 | Kennedy |
| 5,721,973 A | 2/1998 | Mizukawa |
| 5,763,421 A | 6/1998 | Caretto et al. |
| 5,767,269 A | 6/1998 | Hirsh et al. |
| 5,783,570 A | 7/1998 | Yokota et al. |
| 5,808,021 A | 9/1998 | Holme et al. |
| 5,849,721 A | 12/1998 | Uzan |
| 5,912,237 A | 6/1999 | Kennedy |
| 5,922,358 A | 7/1999 | Doutremepuich et al. |
| 5,935,850 A | 8/1999 | Clark et al. |
| 5,958,899 A | 9/1999 | Zoppetti et al. |
| 6,045,805 A | 4/2000 | Moreau |
| 6,075,013 A | 6/2000 | Weitz et al. |
| 6,077,683 A | 6/2000 | Kennedy |
| 6,143,730 A | 11/2000 | Parish et al. |
| 6,197,943 B1 | 3/2001 | Casu et al. |
| 6,217,863 B1 | 4/2001 | Godavarti et al. |
| 6,228,998 B1 | 5/2001 | Miura et al. |
| 6,232,093 B1 | 5/2001 | Van Houdenhoven et al. |
| 6,255,296 B1 | 7/2001 | Daniels |
| 6,258,798 B1 | 7/2001 | Wallentin |
| 6,346,517 B1 | 2/2002 | Wong et al. |
| 6,384,021 B1 | 5/2002 | Mardiguian |
| 6,492,503 B1 | 12/2002 | Kariya et al. |
| 6,617,316 B1 | 9/2003 | Mourier et al. |
| 6,812,221 B2 | 11/2004 | McKeehan et al. |
| RE38,743 E | 6/2005 | Debrie |
| 7,008,933 B2 | 3/2006 | Welzel |
| 7,083,937 B2 | 8/2006 | Sasisekharan et al. |
| 7,390,633 B2 | 6/2008 | Liu et al. |
| 7,575,886 B2 | 8/2009 | Venkataraman et al. |
| 7,585,642 B2 | 9/2009 | Sasisekharan et al. |
| 7,687,579 B2 | 3/2010 | Takahashi et al. |
| 7,790,466 B1 | 9/2010 | Shriver et al. |
| 7,811,827 B2 | 10/2010 | Raguram |
| 7,816,144 B1 | 10/2010 | Shriver et al. |
| 7,968,082 B1 | 6/2011 | Shriver et al. |
| 8,003,402 B2 | 8/2011 | Yamamoto et al. |
| 8,076,149 B1 | 12/2011 | Shriver et al. |
| 8,101,733 B1 | 1/2012 | Shriver et al. |
| 2002/0169143 A1 | 11/2002 | Sasisekharan et al. |
| 2003/0203385 A1 | 10/2003 | Venkataraman et al. |
| 2004/0198697 A1 | 10/2004 | Cohen et al. |
| 2004/0265943 A1 | 12/2004 | Viskov et al. |
| 2005/0119477 A1 | 6/2005 | Mourier et al. |
| 2005/0186679 A1 | 8/2005 | Viskov et al. |
| 2005/0215519 A1 | 9/2005 | Viskov et al. |
| 2005/0288252 A1 | 12/2005 | Nurcombe et al. |
| 2006/0024664 A1 | 2/2006 | Sasisekharan et al. |
| 2006/0182734 A1 | 8/2006 | Liu et al. |
| 2007/0065921 A1 | 3/2007 | Sasisekharan et al. |
| 2007/0098708 A1 | 5/2007 | Myette |
| 2007/0134226 A1 | 6/2007 | Myette |
| 2007/0161073 A1 | 7/2007 | Sasisekharan et al. |
| 2007/0287683 A1 | 12/2007 | Shriver et al. |
| 2008/0009069 A1 | 1/2008 | Mourier et al. |
| 2008/0318328 A1 | 12/2008 | Viskov et al. |
| 2010/0279269 A1 | 11/2010 | Parsons et al. |
| 2011/0207919 A1 | 8/2011 | Beccati et al. |

FOREIGN PATENT DOCUMENTS

| | | |
|---|---|---|
| EP | 380943 B1 | 9/1994 |
| EP | 432537 B1 | 1/1995 |
| EP | 483733 B1 | 8/1996 |
| EP | 623629 B1 | 8/1996 |
| EP | 625166 B1 | 9/1997 |
| EP | 557887 B1 | 12/1997 |
| EP | 708785 B1 | 3/1999 |
| EP | 693499 B1 | 12/1999 |
| EP | 789777 B1 | 8/2000 |
| EP | 970130 B1 | 7/2002 |
| EP | 735050 B1 | 9/2002 |
| EP | 1580197 A1 | 9/2005 |
| EP | 1582531 A1 | 10/2005 |
| EP | 1586588 A1 | 10/2005 |
| JP | 11230935 A | 8/1999 |
| WO | 8809347 A1 | 12/1988 |
| WO | 9003791 A1 | 4/1990 |
| WO | 9914326 A1 | 3/1999 |
| WO | 0065521 A2 | 11/2000 |
| WO | 0129055 A2 | 4/2001 |
| WO | 0223190 A2 | 3/2002 |
| WO | 0232406 A2 | 4/2002 |
| WO | 03078960 A2 | 9/2003 |
| WO | 2004027087 A2 | 4/2004 |
| WO | 2005080438 A1 | 9/2005 |
| WO | 2005090411 A1 | 9/2005 |

OTHER PUBLICATIONS

Kinoshita et al., "Microanalysis of glycosaminoglycan-derived oligosaccharides labeled with a fluorophore 2-aminobenzamide by high-performance liquid chromatography: application to disaccharide composition analysis and exosequencing of oligosaccharides", Analytical Biochem., 1999, vol. 269, pp. 367-378.

Kishimoto et al., "Contaminated heparin associated with adverse clinical events and activation of the contact system", The New England Journal of Medicine, Apr. 23, 2008, vol. 358, No. 23, pp. 2457-2467.

Kishimoto et al., "MII8—A rationally engineered low-molecular-weight heparin designed specifically for the treatment of acute coronary syndromes", Thrombosis and Haemostasis, 1999, vol. 102. No. 5. pp. 900-906.

Kittlesen et al., "Human melanoma patients recognize an HLA-A1-restricted CTL epitope from tyrosinase containing two cysteine residues: implications for tumor vaccine development", J. Immunol., 1998, vol. 160, pp. 2099-2106.

Kobayashi et al., "CD4+ T cells from peripheral blood of a melanoma patient recognize peptides derived from nonmutated tyrosinase", Cancer Research, 1998, vol. 58, pp. 296-301.

Kuhle et al., "Pharmacokinetic study of tinzaparin in pediatric patients", Blood, 2002, vol. 100, No. 11, Abstract No. 3975.

Lamari et al., "Analysis of glycosaminoglycan-derived disaccharides in biologic samples by capillary electrophoresis and protocol for sequencing glycosaminoglycans", Biomedical Chromatography, 2002, vol. 16, pp. 95-102.

Langer "New methods of drug delivery", Science, 1990, vol. 249, pp. 1527-1533.

Larnkjaer et al., "Binding of Low Molecular Weight Heprin (Tinzaparin sodium) to Bovine Endothelial Cells in vitro" Thrombosis Res., vol. 75., No. 2, pp. 185-194 (1994).

Lee et al., "Separation of reduced disaccharides derived from glycosaminoglycans by high-performance liquid chromatography", J. of Chromatography, 1981, vol. 212, pp. 65-73.

Li et al., "Linkage analysis of chromophore-labeled disaccharides and linear oligosaccharides by negative ion fast atom bombardment ionization and collisonal-induced dissociation with B/E scanning", Analyt. Biochem., 1993, vol. 211, No. 2, pp. 250-257.

Lin et al., "Heparan sulfate proteoglycans are essential for FGF receptor signaling during *Drosophila* embryonic development", Development, 1999, vol. 126, pp. 3715-3723.

Lindahl et al., "Common binding sites for b-amyloid fibrils and fibroblast growth factor-2 in heparan sulfate from human cerebral cortex", J. Biol. Chem., 1999, vol. 274, pp. 30631-30635.

Lindhart et al., "Mapping and quantification of the major oligosaccharide components of heparin", Biochem. Journal, 1988, vol. 254, pp. 781-787.

Lindhart et al., "New methodologies in heparin structure analysis and the genereation of LMW heparins", Heparin and Related Polysaccharides, 1992, pp. 37-47, ed. D.A. Lane et al., Plenum Press, New York.

Lindhart et al., "Oligosaccharide mapping of low molecular weight heparins: structure and activity differences", J. of Medicinal Chem., 1990, vol. 33, No. 6, pp. 1639-1645.

Liotta et al., "Cancer metastasis and angiogenesis: an imbalance of positive and negative regulation", Cell, 1991, vol. 64, pp. 327-336.

(56) References Cited

OTHER PUBLICATIONS

Liu et al., "A heparin-binding synthetic peptide of heparin/heparan sulfate-interacting protein modulates blood coagulation activities", PNAS, 1997, vol. 94, pp. 1739-1744.

Liu et al., "Strategy for the sequence analysis of heparin", Glycobiology, 1995, vol. 5, pp. 765-774.

Lou et al., "Structural Specificity in a FGF7-Affinity Purified Heparin Octasaccharide Required for Formation of a Complex with FGF7 and FGFR2IIIb" Journal of Cellular Biochemistry, vol. 97, pp. 1241-1258 (2006).

Lupetti et al., "Translation of a retained intron in tyrosinase-related protein (TRP) 2 mRNA generates a new cytotoxic T lymphocyte (CTL)-defined and shared human melanoma antigen not expressed in normal cells of the melanocytic lineage", J. Exp. Med., 1998, vol. 188, pp. 1005-1016.

Malsch et al., "High-resolution capillary electrophoresis and polyacrylamide gel electrophoresis of heparins," Journal of Chromatography A, 1995, vol. 716, pp. 258-268.

Mandruzzato et al., "A CASP-8 mutation recognized by cytolytic T lymphocytes on a human head and neck carcinoma", J. Exp. Med., 1997, vol. 186, pp. 785-793.

Manici et al., "Melanoma cells present a MAGE-3 epitope to CD4(+) cytotoxic T cells in association with histocompatibility leukocyte antigen DR11", J. Exp. Med., 1999, vol. 189, pp. 871-876.

Mascellani et al., "Characterization of di- and monosulfated, unsaturated heparin disaccharides with terminal N-sulfated 1,6-anhydro-b-D-glucosamine or N-sulfated 1,6-anydro-b-D-mannosamine residues", Carbohydrate Research, 2007, vol. 342, pp. 835-842.

Mauray et al., "Mechanism of factor IXa inhibition by antithrombin in the presence of unfractionated and low molecular weight heparins and fucoidan", Biochim. Biophys. Acta, vol. 1387, No. 1-2, pp. 184-194, (1998).

McLaurin et al., "Interactions of Alzheimer amyloid-b peptides with glycosaminoglycans effects on fibril nucleation and growth", Eur. J. Biochem., 1999, vol. 266, pp. 1101-1110.

Merchant et al., "Structure of heparin-derived tetrasaccharides", Biochem. Journal, 1985, vol. 229, pp. 369-377.

Merry et al., "Highly sensitive sequencing of the sulfated domains of heparan sulfate", J. Biol. Chem., 1999, vol. 274, pp. 18455-18462.

Militsopoulou et al., "Determination of twelve heparin- and heparan sulfate-derived disaccharides as 2-aminoacridone derivatives by capillary zone electrophoresis using ultrviolet and laser-induced flourescence detection", Electrophoresis, 2002, vol. 23, pp. 1104-1109.

Morel et al., "A tyrosinase peptide presented by HLA-B35 is recognized on a human melanoma by autologous cytotoxic T lymphocytes", Int. J. Cancer, 1999, vol. 83, pp. 755-759.

Morell et al., "Analysis of starch structure using fluorophore-assisted carbohydrate electrophoresis", Electrophoresis, 1998, vol. 19, No. 15, pp. 2603-2611.

Oiso et al., "A newly identified MAGE-3-derived epitope recognized by HLA-A24-restricted cytotoxic T lymphocytes", Int. J. Cancer, 1999, vol. 81, pp. 387-394.

Parish et al., "A basement-membrane permeability assay which correlates with the metastatic potential of tumour cells", Int. J. Cancer, 1992, vol. 52, pp. 378-383.

Park et al., "Purification and characterization of heparin sulphate proteoglycan from bovine brain", Biochem. Journal, 1999, vol. 344, pp. 723-730.

Parkhurst et al., Identification of a shared HLA-A*0201-restricted T-cell epitope from the melanoma antigen tyrosinase-related protein 2 (TRP2)'', Cancer Research, 1998, vol. 58, pp. 4895-4901.

Perlin et al., "Spectroscopic methods", The Polysaccharides, 1982, vol. 1, pp. 133-193, Edited by G.O., Academic Press.

Pervin et al., "Separation of glycosaminoglycan-derived oligosaccharides by capillary electrophoresis using reverse polarity", Analytical Biochem., 1994, vol. 221, pp. 182-188.

Petitou et al., "Synthetic oligosaccharides having various functional domains: potent and potentially safe heparin mimetics", Bioorg. Med. Chem. Lett., 1999, vol. 9, No. 8, pp. 1161-1166.

Piani et al., "Alkali-induced optical rotation changes in heparins and heparan sulfates, and their relation to iduronic acid-containing sequences", Journal of Carbohydrate Chemistry, 1993, vol. 12, No. 4&5, pp. 507-521.

Pieper et al., "Biochemical identification of a mutated human melanoma antigen recognized by CD4(+) T cells", J. Exp. Med., 1999, vol. 189, pp. 757-765.

Plaintiffs' Answer to Defendants' Counterclaims—*Momenta Pharmaceuticals, Inc. and Sandoz, Inc.*, Plaintiffs, v. *Amphastar Pharmaceuticals, Inc., International Medication Systems, Ltd., Watson Pharmaceuticals, Inc., and Watson Pharma, Inc.*, Defendants. 2012 WL 4060946.

Plaintiffs' Claim Construction Memorandum U.S. Patent No. 7,575,886 *Momenta Pharmaceuticals, Inc. and Sandoz Inc.*, Plaintiffs, v. *Teva Pharmaceuticals USA, Inc.*, Defendant. *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 2455758.

Plaintiffs' Claim Construction Memorandum U.S. Patent No. 7,575,886 *Momenta Pharmaceuticals, Inc. and Sandoz Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL6150688.

Plaintiffs' Claim Construction Memorandum U.S. Patent No. 7,575,886 *Momenta Pharmaceuticals, Inc. and Sandoz Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150798.

Plaintiffs' Claim Construction Memorandum U.S. Patent No. 7,790,466 *Momenta Pharmaceuticals, Inc. and Sandoz Inc.*, Plaintiffs, v. *Teva Pharmaceuticals USA, Inc.*, Defendant, *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 2455750.

Plaintiffs' Claim Construction Memorandum U.S. Patent No. 7,790,466 *Momenta Pharmaceuticals, Inc. and Sandoz, Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150684.

Plaintiffs' Reply to the Defendants' Claim Construction Memoranda Regarding U.S. Patent No. 7,790,466 *Momenta Pharmaceuticals, Inc. and Sandoz Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150797.

Pojasek, et al., "Histidine 295 and histidient 510 are crucial for the enzymatic degradation of heparan sulfate by heparinase III", Biochemistry, 2000, vol. 39, pp. 4012-4019.

Razi et al., "Structural and functional properties of heparin analogues obtained by chemical sulphation of *Escherichia coli* K5 capsular polysaccharide", Biochem. J., vol. 309, No. 2, pp. 465-475.

Reply Brief for Appellants, *Momenta Pharmaceuticals, Inc.*, Plaintiff-Appellee, *Sandoz, Inc.*, Plaintiff-Appellee, v. *Amphastar Pharmaceuticals, Inc., International Medication Systems, Ltd., Watson Pharmaceuticals' Inc. and Watson Pharma, Inc.*, Defendants-Appellants. 2011 WL 7039088.

Reply Brief for Petitioners—*Momenta Pharmaceuticals, Inc.* v. *Amphastar Pharmaceuticals, Inc.* 2013 WL 2428972.

Rhomberg et al., "Mass spectrometric and capillary electrophoretic investigation of the enzymatic degradation of heparin-like glycosaminoglycans", PNAS, 1998, vol. 95, pp. 4167-4181.

(56) References Cited

OTHER PUBLICATIONS

Rhomburg et al., "Mass spectrometric evidence for the enzymatic mechanism of the depolymerization of heparin-like glycosaminoglycans by heparinase II", PNAS USA, 1998, vol. 95, pp. 12232-12237.

Rice et al., "Gradient page and strong anion exchange Sax Hplc as analytical tools for sequencing the heparin polymer", American Chemical Society, 1987, vol. 193, pp. 1, Abstracts of paper from the National Meeting.

Rice et al., "High-performance liquid chromatographic separation of heparin-derived oligosaccharides", Analytical Biochem., 1985, vol. 150, No. 2, pp. 325-331.

Robbins et al., "A mutated b-catenin gene encodes a melanoma-specific antigen recognized by tumor infiltrating lymphocytes", J. Exp. Med., 1996, vol. 183, pp. 1185-1192.

Robbins et al., "The intronic region of an incompletely spliced gp100 gene transcript encodes an epitope recognized by melanoma-reactive tumor-infiltrating lymphocytes", J. Immunol., 1997, vol. 159, pp. 303-308.

Ronsin et al., "A non-AUG-defined alternative open reading frame of the intestinal carboxyl esterase mRNA generates an epitope recognized by renal cell carcinoma-reactive tumor-infiltrating lymphocytes in situ", J. Immunol., 1999, vol. 163, pp. 483-490.

Rota et al, "Free radical generation during chemical depolymerization of heparin", Analytical Biochemistry, vol. 344, pp. 193-203 (2005).

Ruiz-Calero et al., "Pressure-assisted capillary electrophoresis-electrospray ion trap mass spectrometry for the analysis of heparin depolymerised disaccharides", J. of Chromatogrphy A, 2001, vol. 914, pp. 277-291.

Ruiz-Calero et al., "Use of reversed polarity and pressure gradient in the analysis of disaccharide composition of heparin by capillary electrophoresis", J. of Chromatography A, 1998, vol. 828, pp. 497-508.

Röpke et al., "Spontaneous human squamous cell carcinomas are killed by a human cytotoxic T lymphocyte clone recognizing a wild-type p53-derived peptide", Proc. Natl. Acad. Sci. USA, 1996, vol. 93, pp. 14704-14707.

Saad et al., "Compositional analysis and quantification of heparin and heparan sulfate by electrospray ionization ion trap mass spectrometry", Anal. Chem., 2003, vol. 75, pp. 2985-2995.

Sasisekharan et al. "Heparinase inhibits neovascularization", Proc. Natl. Acad. Sci. USA, 1994, vol. 91, pp. 1524-1528.

Scapol et al., "Capillary electrophoresis of heparin and dermatan sulfate unsaturated disaccharides with triethylamine and acetonitrile as electrolyte additives", J. of Chromatography A, 1996, vol. 735, pp. 367-374.

Schanda, "Very fast two-dimensional NMR spectroscopy for real-time investigation of dynamic events in proteins on the time scale of seconds", Journal of the American Chemical Society, 2005, vol. 127, pp. 8014-8015.

Schneider et al., "Overlapping peptides of melanocyte differentiation antigen Melan-A/MART-1 recognized by autologous cytolytic T lymphocytes in association with HLA-B45.1 and HLA-A2.1", Int. J. Cancer, 1998, vol. 75, pp. 451-458.

Shriver et al., "Cleavage of the antithrombin III binding site in heparin by heparinases and its implication in the generation of low molecular weight heparin", PNAS, 2000, vol. 97, No. 19, pp. 10365-10370.

Shriver et al., "Sequencing of 3-0 sulfate containing heparin decasaccharides with a partial antithrombin III binding site", PNAS, 2000, vol. 97, No. 19, pp. 10359-10364.

Skipper et al., "An HLA-A2-restricted tyrosinase antigen on melanoma cells results from posttranslational modification and suggests a novel pathway for processing of membrane proteins", J. Exp. Med., 1996, vol. 183, pp. 527-534.

Skipper et al., "Shared epitopes for HLA-A3-restricted melanoma-reactive human CTL include a naturally processed epitope from Pmel-17/gp100", J. Immunol., 1996, vol. 157, pp. 5027-5033.

Sudor et al., "End-label free-solution electrophoresis of the low molecular weight heparins", Anal. Chem., 1997, vol. 69, No. 16, pp. 3199-3204.

Sundaram et al., "Rational design of low-molecular weight heparins with improved in vivo activity," PNAS, Jan. 21, 2003, vol. 100, No. 2, pp. 651-656.

Supplemental Partial European Search Report from European Application No. EP 037446289 dated Jul. 14, 2008.

Tahara et al., "Identification of a MAGE-2-encoded human leukocyte antigen-A24-binding synthetic peptide that induces specific antitumor cytotoxic T lymphocytes", Clin. Cancer Res., 1999, vol. 5, pp. 2236-2241.

Tanaka et al., "Induction of antitumor cytotoxic T lymphocytes with a MAGE-3-encoded synthetic peptide presented by human leukocytes antigen-A24", Cancer Res., 1997, vol. 57, pp. 4465-4468.

Tanzarella et al., "Identification of a promiscuous T-cell epitope encoded by multiple members of the MAGE family", Cancer Res., 1999, vol. 59, pp. 2668-2674.

Thanawiroon et al., "Liquid chromatography/mass spectrometry sequencing approach for highly sulfated heparin-derived oligosaccharides", J. of Biological Chem., 2004, vol. 279, No. 4, pp. 2608-2615.

Thanawiroon et al., "Separation of a complex mixture of heparin-derived oligosaccharides using reversed-phase high-performance liquid chromatography", J. of Chromatography A, 2003, vol. 1014, pp. 215-223.

Toida et al., "Structural differences and the presence of unsubstituted amino groups in heparan sulphates from different tissues and species", Biochem. Journal, 1997, vol. 322, pp. 499-506.

Topalian et al., "Melanoma-specific CD4+ T cells recognize nonmutated HLA-DR-restricted tyrosinase epitopes", J. Exp. Med., 1996, vol. 183, pp. 1965-1971.

Toyoda et al., "Rapid and sensitive analysis of disaccharide composition in heparin and heparan sulfate by reversed-phase ion-pair chromatography on a 2 mm porous silica gel column", J. of Chromatography A, 1999, vol. 830, pp. 197-201.

Traversari et al., "A nonapeptide encoded by human gene MAGE-1 is recognized on HLA-A1 by cytolytic T lymphocytes directed against tumor antigen MZ2-E", J. Exp. Med., 1992, vol. 176, pp. 1453-1457.

Trehy et al., "Analysis of heparin sodium by SAX/HPLC for contaminants and impurities", Journal of Pharmaceutical and Biomedical Analysis, 2009, vol. 49, No. 3, pp. 671-673.

Tsai et al., "Identification of subdominant CTL epitopes of the GP100 melanoma-associated tumor antigen by primary in vitro immunization with peptide-pulsed dendritic cells", J. Immunol., 1997, vol. 158, pp. 1796-1802.

Tsang et al., "Generation of human cytotoxic T cells specific for human carcinoembryonic antigen epitopes from patients immunized with recombinant vaccinia-CEA vaccine", J. Natl. Cancer Inst., 1995, vol. 87, pp. 982-990.

Tsuda et al., "The cell-surface proteoglycan Daily regulates Wingless signalling in *Drosophila*", Nature, 1999, vol. 400, pp. 276-280.

Turnbull et al., "A strategy for rapid sequencing of heparan sulfate and heparin saccharides", Proc. Natl. Acad. Sci. USA, 1999, vol. 96, pp. 2698-2703.

Turnbull et al., "Analytical and preparative strong anion-exchange HPLC of heparan sulfate and heparin saccharides" Methods in Molecular Biology, vol. 171, pp. 141-147 (2001).

Van Den Eynde et al., "A new family of genes coding for an antigen recognized by autologous cytolytic T lymphocytes on a human melanoma", J. Exp. Med., 1995, vol. 182, pp. 689-698.

Van Der Bruggen et al., "A peptide encoded by human gene MAGE-3 and presented by HLA-A2 induces cytolytic T lymphocytes that recognize tumor cells expressing MAGE-3", Eur. J. Immunol., 1994, vol. 24, pp. 3038-3043.

Van Der Bruggen et al., "Autologous cytolytic T lymphocytes recognize a MAGE-1 nonapeptide on melanomas expressing HLA-Cw*1601", Eur. J. Immunol., vol. 24, pp. 2134-2140.

Van Putten et al., Determination of low molecular weight heparin in clinical laboratory, Haemostasis, 1984, vol. 14, pp. 205-210.

Venkataraman et al., "Sequencing complex polysaccharides", Science, 1999, vol. 286, pp. 537-542.

(56) References Cited

OTHER PUBLICATIONS

Volpi et al., "Characterization of heparins with different relative molecular masses (from 11 600 to 1600) by various analytical techniques", J. of Chromatography, 1993, vol. 622, pp. 13-20.
Volpi et al., "Hyaluronic acid and chondroitin sulfate unsaturated disaccharides analysis by high-performance liquid chromatography and fluorimetric detection with dansylhydrazine", Analytical Biochem., 2002, vol. 277, pp. 19-24.
Vonderheide et al., "The telomerase catalytic subunit is a widely expressed tumor-associated antigen recognized by cytotoxic T lymphocytes", Immunity, 1999, vol. 10, pp. 673-679.
Vynios et al., "Advances in analysis of glycosaminoglycans: its applications for the assessment of physiological and pathological states of connective tissues", J. of Chromatography B, 2002, vol. 781, pp. 21-38.
Desai et al., "Oligosaccharide composition of heparin and low-molecular-weight heparin by capillary electrophoresis", Analytical Biochem., 1993, vol. 213, pp. 120-127.
Desai et al., "Molecular weight of low molecular weight heparins by 13C nuclear magnetic resonance spectroscopy", Carbohydrate Research, 1994, vol. 255, pp. 193-212.
Docket 1:10cv12079—*Momenta Pharmaceuticals, Inc. et al v. Teva Pharmaceuticals Industries Ltd. et al.*
Docket 1:11cv11681—*Momenta Pharmaceuticals, Inc. et al v. Amphastar Pharmaceuticals, Inc. et al.*
Drummond et al., "Electrophoretic sequencing of heparin/heparan sulfate oligosaccharides using a highly sensitive fluorescent end label", Proteomics, 2001, vol. 1, No. 2, pp. 304-310.
Duffour et al., "A MAGE-A4 peptide presented by HLA-A2 is recognized by cytolytic T lymphocytes", Eur. J. Immunol., 1999, vol. 29, pp. 3329-3337.
Ernst et al., "Direct evidence for a predominantly exolytic processive mechanism for depolymerization of heparin-like glycosaminoglycans by heparinase I", PNAS USA, 1998, vol. 95, pp. 4182-4187.
Ernst et al., "Expression in *Escherichia coli*, purification and characterization of heparinase I from Flavobacterium heparinum", Biochem. J., 1996, vol. 315, pp. 589-597.
European Search Report from European Application No. 10190250.0 dated Dec. 27, 2010.
Fareed et al., "Generic low-molecular-weight heparins: some practical considerations" Seminars in Thrombosis and Hemostasis, 2004, vol. 30, No. 6, pp. 703-713.
Fareed et al., "Biochemical and pharmacologic heterogeneity in low molecular weight heparins. Impact on the therapeutic profile", Current Pharmaceutical Design, 2004, vol. 10, pp. 983-999.
Fisk et al., "Identification of immunodominant peptide of HER-2/neu protooncogene recognized by ovarian tumor-specific cytotoxic T lymphocyte lines", J. Exp. Med., 1995, vol. 181, pp. 2109-2117.
Franz et al., "MALDI-FTMS characterization of oligosaccharides labeled with 9-aminofluorene", J. Am. Soc. Mass Spectrom., 2001, vol. 12, No. 12, pp. 1254-1261.
Fujie et al., "A MAGE-1-encoded HLA-A24-binding synthetic peptide induces specific anti-tumor cytotoxic T lymphocytes", Int. J. Cancer, 1999, vol. 80, pp. 169-172.
Gaudin et al., "A hsp70-2 mutation recognized by CTL on a human renal cell carcinoma", J. Immunol., 1999, vol. 162, pp. 1730-1738.
Gaugler et al., "Human gene MAGE-3 codes for an antigen recognized on a melanoma by autologous cytolytic T lymphocytes", J. Exp. Med., 1994, vol. 179, pp. 921-930.
Gjertsen et al., "Cytotoxic CD4+ and CD8+ T lymphocytes, generated by mutant p21-ras (12Val) peptide vaccination of a patient, recognize 12Val-dependent nested epitopes present within the vaccine peptide and kill autologous tumour cells carrying this mutation", Int. J. Cancer, 1997, vol. 72, pp. 784-790.
Guerrini et al., "Combined quantitative 1H and 13C nuclear magnetic resonance spectroscopy for characterization of heparin preparations", Seminars in Thrombosis and Hemostasis, 2001, vol. 27, No. 5, pp. 473-482.
Guerrini et al., "Complex glycosaminoglycans: profiling substitution patterns by two-dimensional nuclear magnetic resonance spectroscopy", Analytical Biochemistry, 2005, vol. 337, pp. 35-47.
Guerrini et al., "Low molecular weight heparins: structural differentiation by bidimensional nuclear magnetic resonance spectroscopy", Seminars in Thrombosis and Hemostasis, 2007, vol. 33, No. 5, pp. 478-487.
Guerrini et al., "Oversulfated chondroitin sulfate is a contaminant in heparin associated with adverse clinical events", Nature Biotechnology, Jun. 2008, vol. 26, No. 6, pp. 669-675, Nature Publishing Group US.
Guilloux et al., "A peptide recognized by human cytolytic T lymphocytes on HLA-A2 melanomas is encoded by an intron sequence of the N-acetylglucosaminyltransferase V gene", J. Exp. Med., 1996, vol. 183, pp. 1173-1183.
Guizzardi et al., "Pharmacokinetics and organ distribution in rats of a low molecular weight heparin", Arzneimittel-Forschung, 1987, vol. 37, No. 11, pp. 1281-1283.
Guo et al., "The disaccharide composition of heparins and heparan sulfates", Analytical Biochem., 1989, vol. 176, pp. 96-104.
Guéguen et al., "An antigen recognized by autologous CTLs on a human bladder carcinoma", J. Immunol., 1998, vol. 160, pp. 6188-6194.
Harenberg et al., "Overview on guidelines and recommendations for generic low-molecular-weight heparins", Thrombosis Research, vol. 127, S100-S104 (2011).
Hennekens et al., "Current issues concerning thrombolytic therapy of acute myocardial infarction", J. Am. Coll. Cardiol., 1995, vol. 25, No. 7, pp. 18S-22S.
Herman et al., "A peptide encoded by the human MAGE3 gene and presented by HLA-B44 induces cytolytic T lymphocytes that recognize tumor cells expressing MAGE3", Immunogenetics, 1996, vol. 43, pp. 377-383.
Hirano, "NMR study of 4-deoxy-a-L-threo-4-enohexopyranosyluronic acid (1® 3)2-acetamido-2-deoxy-D-hexoses produced in the enzymic digestion of hyaluronate, chondroitin and chondroitin sulfates", Organic Magnetic Resonance, vol. 2, pp. 577-580.
Hogan et al., "The peptide recognized by HLA-A68.2-restricted, squamous cell carcinoma of the lung-specific cytotoxic T lymphocytes is derived from a mutated elongation factor 2 gene", Cancer Res., 1998, vol. 58, pp. 5144-5150.
Holmes et al., "Lessons we have learned from the GUSTO trial", J. Am. Coll. Cardiol., 1995, vol. 25, No. 7, pp. 10S-17S.
Holzgrabe et al., "Quantitative NMR spectroscopy—Applications in drug analysis", Journal of Pharmaceutical and Biomedical Analysis, vol. 38, pp. 806-812.
Hricovini et al., "Conformational analysis of heparin epoxide in aqueous solution. An NMR relaxation study", Carbohydrate Research, 1995, vol. 277, pp. 11-23.
Huang et al., "Cytolytic T lymphocytes recognize an antigen encoded by MAGE-A10 on a human melanoma", J. Immunol., 1999, vol. 162, pp. 6849-6854.
Ikeda et al., "Characterization of an antigen that is recognized on a melanoma showing partial HLA loss by CTL expressing an NK inhibitory receptor", Immunity, 1997, vol. 6, pp. 199-208.
Imai et al., "Directional degradation of b-chitin by chitinase A1 revealed by a novel reducing end labelling technique", FEBS Lett, 2002, vol. 510, No. 3, pp. 201-205.
Imanari et al., "High-performance liquid chromatographic analysis of glycosaminglycan-derived oligosaccharides", J. of Chomatography A, 1996, vol. 720, pp. 275-293.
International Search Report and Written Opinion from International Application Serial No. PCT/US11/21582 mailed Mar. 21, 2011.
International Search Report and Written Opinion from International Application Serial No. PCT/US2009/055792 mailed Feb. 12, 2009.
International Search Report from International Application Serial No. PCT/US03/07208 dated Nov. 16, 2004.
Jeske et al., "Pharmacologic profile of certoparin", Exp. Opin. Invest. Drugs, 1999, vol. 8, No. 3, pp. 315-327.

(56) References Cited

OTHER PUBLICATIONS

Jäger et al., "Simultaneous humoral and cellular immune response against cancer-testis antigen NY-ESO-1: definition of human histocompatibility leukocyte antigen (HLA)-A2-binding peptide epitopes", J. Exp. Med., 1998, vol. 187, pp. 265-270.

Kang et al., "Identification of a tyrosinase epitope recognized by HLA-A24-restricted, tumor-infiltrating lymphocytes", J. Immunol., 1995, vol. 155, pp. 1343-1348.

Karamanos et al., "Ion-pair high-performance liquid chromatography for determining disaccharide composition in heparin and heparan sulphate", J. of Chromatography, 1997, vol. 765, pp. 169-179.

Kariya et al., "Disaccharide analysis of heparin and heparan sulfate using deaminative cleavage with nitrous acid and subsequent labeling with paranitrophenyl hydrazine", J. Biochem., 1998, vol. 123, No. 2, pp. 240-246, Tokyo.

Kawakami et al., "Identification of a human melanoma antigen recognized by tumor-infiltrating lymphocytes associated with in vivo tumor rejection", Proc. Natl. Acad. Sci. USA, 1994, vol. 91, pp. 6458-6462.

Kawakami et al., "Identification of new melanoma epitopes on melanosomal proteins recognized by tumor infiltrating T lymphocytes restricted by HLA-A1, -A2, and -A3 alleles", J. Immunol., 1998, vol. 161, pp. 6985-6992.

Kawakami et al., "Identification of the immunodominant peptides of the MART-1 human melanoma antigen recognized by the majority of HLA-A2-restricted tumor infiltrating lymphocytes", J. Exp. Med., 1994, vol. 180, pp. 347-352.

Kawakami et al., "Recognition of multiple epitopes in the human melanoma antigen gp100 by tumor-infiltrating T lymphocytes associated with in vivo tumor regression", J. Immunol., 1995, vol. 154, pp. 3961-3968.

Kawashima et al., "The multi-epitope approach for immunotherapy for cancer: identification of several CTL epitopes from various tumor-associated antigens expressed on solid epithelial tumors", Hum. Immunol., 1998, vol. 59, pp. 1-14.

"2.6.26. Test for anti-D antibodies in intravenous immunglobulin", Pharmeuropa, Jan. 2004, vol. 16, No. 1, pp. 121-122.

Aarnoudse et al., "Interleukin-2-induced, melanoma-specific T cells recognize CAMEL, an unexpected translation product of LAGE-1" Int. J. Cancer, 1999, vol. 82, pp. 442-448.

Alban et al., "Development of SPC-ELISA: a new assay principle for the study of sulfated polysaccharide-protein interactions", Journal of Biomolecular Screening, 2001, vol. 6, No. 6, pp. 393-400.

Amended Complaint—*Momenta Pharmaceuticals, Inc. and Sandoz Inc.*, Plaintiffs, v. *Amphastar Pharmaceuticals, Inc., International Medication Systems, Ltd., Watson Pharmaceuticals, Inc., and Watson Pharma, Inc.*, Defendants. 2011 WL 9556659.

Ampofo et al., "Disaccharide compositional analysis of heparin and heparan sulfate using capillary zone electrophoresis", Analytical Biochemistry, 1991, vol. 199, pp. 249-255.

Ansel et al., "Pharmaceutical dosage forms and drug delivery systems", 1999, pp. 23-27 and 54-59, published by Lippincott Williams & Wilkins.

Anumula et al., "High resolution and high sensitivity methods for oligosaccharide mapping and characterization by normal phase high performance liquid chromatography following derivatization with highly fluorescent anthranilic acid", Glycobiology, 1998, vol. 8, No. 7, pp. 685-694.

Araki et al., "Application of 2-aminopyridine fluorescence labeling in the analysis of in vivo and in vitro metabolism of dextran sulfate sodium by size-exclusion high-performance liquid chromatorgraphy", J. Chromatography B Biomed. Sci., 2001, vol. 753, No. 2, pp. 209-215.

Bartolucci et al., "Inhibition of human leukocyte elastase by chemically and naturally oversulfated galactosaminoglycans", Carbohydrate Research, 1995, vol. 276, No. 2, pp. 401-408.

Bennett et al., "High resolution analysis of functional determinants on human tissue-type plasminogen activator", J. of Biological Chemistry, 1991, vol. 266, No. 8, pp. 5191-5201.

Bianchini et al., "Few bicyclic acetals at reducing end of low-molecular-weight heparins: might they restrict specification of pharmacopoeia?" Pharmeuropa Scientific Notes, 2005, vol. 1, pp. 1-3.

Bianchini et al., "Variability of heparins and heterogeneity of low molecular weight heparins" Seminars in Thrombosis and Hemostasis, 2007, vol. 33, No. 5, pp. 496-502.

Bigge et al., "Nonselective and efficient fluorescent labeling of glycans using 2-amino benzamide and anthranilic acid", Anal. Biochem., 1995, vol. 230, No. 2, pp. 229-238.

Binari et al., "Genetic evidence that heparin-like glycosaminoglycans are involved in wingless signaling", Development, 1997, vol. 124, pp. 2623-2632.

Bosch et al., "Recognition of BCR-ABL positive leukemic blasts by human CD4+ T cells elicited by primary in vitro immunization with a BCR-ABL breakpoint peptide", Blood, 1996, vol. 88, pp. 3522-3527.

Bottio et al., "Life threatening anaphylactic shock caused by porcine heparin intravenous infusion during mitral valve repair," The Journal of Thoracic and Cardiovascular Surgery, 2003, vol. 126, pp. 1194-1195.

Boël et al. "BAGE: a new gene encoding an antigen recognized on human melanomas by cytolytic T lymphocytes", Immunity, 1995, vol. 2, pp. 167-175.

Brichard et al., "A tyrosinase nonapeptide presented by HLA-B44 is recognized on a human melanoma by autologous cytolytic T lymphocytes", Eur. J. Immunol., 1996, vol. 26, pp. 224-230.

Brief for Appellants—*Momenta Pharmaceuticals, Inc.*, Plaintiff-Appellee, *Sandoz, Inc*, Plaintiff-Appellee, v. *Amphastar Pharmaceuticals, Inc., International Medication Systems, Ltd., and Watson Pharmaceuticals, Inc.*, Defendants-Appellants. 2011 WL 7111556.

Brief in Opposition—*Momenta Pharmaceuticals, Inc.* v. *Amphastar Pharmaceuticals, Inc.* 2013 WL 2316705.

Brief of Plaintiffs—Appellees *Momenta Pharmaceuticals, Inc. and Sandoz, Inc—Momenta Pharmaceuticals, Inc.*, Plaintiff-Appellee, *Sandoz, Inc.*, Plaintiff-Appellee, v. *Amphastar Pharmaceuticals, Inc., International Medication Systems, Ltd., Watson Pharmaceuticals, Inc. and Watson Pharma, Inc.*, Defendants-Appellants. 2011 WL 7039087.

Brossart et al., "Her-2/neu-derived peptides are tumor-associated antigens expressed by human renal cell and colon carcinoma lines and are recognized by in vitro induced specific cytotoxic T lymphocytes", Cancer Res., 1998, vol. 58, pp. 732-736.

Brändle et al., "A mutated HLA-A2 molecule recognized by autologous cytotoxic T lymphocytes on a human renal cell carcinoma", J. Exp. Med., 1996, vol. 183, pp. 2501-2508.

Campbell, S. A., Filed by Amphastar pharmaceuticals in response to citizen petition docket No. 03P-0064/CP1 filed with the United States Food and Drug Administration. Response filed on May 13, 2004, Entered into FDA docket system on Jun. 8, 2004.

Carlson et al., "The Determination of recombinant human tissue-type plasminogen activator activity by turbidimetry using a microcentrifugal analyzer", Analytical Biochem., 1988, vol. 168, pp. 428-435.

Castelli et al., "Mass spectromic identification of a naturally processed melanoma peptide recognized by CD8+ cytotoxic T lymphocytes", J. Exp. Med., 1995, vol. 181, pp. 363-368.

Castelli et al., "Novel HLA-Cw8-restricted T cell epitopes derived from tyrosinase-related protein-2 and gp100 melanoma antigens", J. Immunol., 1999, vol. 162, pp. 1739-1748.

Cerny et al., "Preparation of 2-amino-1,6-anhydro-2,3-dideoxy-b-D-arabino-hexopyranose. 1H- and 13C-N.M.R. spectra of deoxy derivatives of 2-amino-1,6-deoxy-D-glucose and 2-amino-1,6-anhydro-2-deoxy-D-mannose", Carbohydrate Research, 1984, vol. 130, pp. 103-114.

Chaux et al. "Identification of five MAGE-A1 epitopes recognized by cytolytic T lymphocytes obtained by in vitro stimulation with dendritic cells transduced with MAGE-A1", J. Immunol., 1999, vol. 163, pp. 2928-2936.

Chaux et al., "Identification of MAGE-3 epitopes presented by HLA-DR molecules to CD4(+) T lymphocytes", J. Exp. Med., 1999, vol. 189, pp. 767-778.

(56) References Cited

OTHER PUBLICATIONS

Chiari et al., "Two antigens recognized by autologous cytolytic T lymphocytes on a melanoma result form a single point mutation in an essential housekeeping gene", Cancer Res., 1999, vol. 59, pp. 5785-5792.

Citizens Petition filed with the United Staes Food and Drug Administration by Aventis Pharmaceuticals Inc. on Feb. 19, 2003.

Citizens Petition Supplemental filed with the United Staes Food and Drug Administration by Aventis Pharmaceuticals Inc. on Feb. 12, 2004.

Collard et al., "A novel approach to 14C lable N-linked oligosaccharides" Analyt. Biochem., 1997, vol. 247, No. 2, pp. 448-450.

Complaint—*Momenta Pharmaceuticals, Inc. and Sandoz Inc.*, Plaintiffs, v. *Amphastar Pharmaceuticals, Inc., International Medication Systems, Ltd. and Watson Pharmaceuticals, Inc.*, Defendants. 2011 WL 4592253.

Complaint—*Momenta Pharmaceuticals, Inc. and Sandoz Inc.*, Plaintiffs, v. *Teva Pharmaceuticals Industries Ltd and Teva Pharmaceuticals USA, Inc.*, Defendants. 2010 WL 4888034.

Correale et al., "In vitro generation of human cytotoxic T lymphocytes specific for peptides derived from prostate-specific antigen", J. Natl. Cancer Inst., 1997, vol. 89, pp. 293-300.

Corrected Brief for Appellants—*Momenta Pharmaceuticals, Inc.*, Plaintiff-Appellee, *Sandoz, Inc.*, Plaintiff-Appellee, v. *Amphastar Pharmaceuticals, Inc., International Medication Systems, Ltd., and Watson Pharmaceuticals, Inc.* Defendants-Appellants. 2011 WL 7111557.

Coulie et al., "A mutated intron sequence codes for an antigenic peptide recognized by cytolytic T lymphocytes on a human melanoma", Proc. Natl. Acad. Sci., 1995, vol. 92, pp. 7976-7980.

Coulie, "Antigens recognized on human tumors by cytolytic T lymphocytes: towards vaccination?", Stem Cells, 1995, vol. 13, pp. 393-403.

Cox et al., "Identification of a peptide recognized by five melanoma-specific human cytotoxic T cell lines", Science, 1994, vol. 264, pp. 716-719.

Da Col et al., "Characterization of the chemical structure of sulphated glycosaminoglycans after enzymatic digestion; Application for liquid chromatography-mass spectrometry with an atmospheric pressure interface", J. of Chromatography, 1993, vol. 647, pp. 289-300.

Dalmora et al., "Biological potency and physicochemical characterization of unfractionated heparins," Revista Brasileira de Hematologi e Hematerapia, 2009, vol. 31, No. 4, pp. 1-7.

Dawes et al., "The measurement of heparin and other therapeutic sulphated polysaccharides in plasma, serum and urine", Thrombosis and Haemostasis, 1985, vol. 54, No. 3, pp. 630-634.

De Backer et al., "Characterization of the GAGE genes that are expressed in various human cancers and in normal testis", Cancer Res., 1999, vol. 59, pp. 3157-3165.

Defendant Amphastar's Opening Claim Construction Brief—*Momenta Pharmaceuticals, Inc. and Sandoz, Inc.*, Plaintiffs, v. *Amphastar Pharmaceuticals, Inc., International Medication Systems, Ltd. and Watson Pharamceuticals, Inc.*, Defendants. 2012 WL 6150799.

Defendant Teva's Reply Claim Construction Brief—*Momenta Pharmaceuticals, Inc. and Sandoz, Inc.*, Plaintiffs, v. *Teva Pharmaceuticals USA, Inc.*, Defendant. 2012 WL 2455760.

Defendants Preliminary Claim Construction Brief *Momenta Pharmaceuticals, Inc. and Sandoz, Inc.*, Plaintiffs, v. *Teva Pharmaceuticals USA, Inc.* Defendant. 2012 WL 2455754.

Defendants' Amended Answer to Plaintiffs' Amended Complaint—*Momenta Pharmaceuticals, Inc., et al.*, Plaintiffs, v. *Amphastar Pharmaceuticals, Inc., et al.*, Defendants. 2012 WL 6150795.

Defendants' Answer to Plaintiffs' Amended Complaint—*Momenta Pharmaceuticals, In., et al.*, Plaintiffs, v. *Amphastar Pharmaceuticals, Inc., et al.*, Defendants. 2012 WL 6150796.

Mulloy et al., "The effect of variation of substitution on the solution conformation of heparin: a spectroscopic and milecular modeling study" Carbohydrate Research, vol. 255, pp. 1-26 (1994).

Wang et al. "Cloning genes encoding MHC Claa II-restricted antigens: mutated CDC27 as a tumor antigen", Science, 1999, vol. 284, pp. 1351-1354.

Wang et al., "A breast and melanoma-shared tumor antigen: T cell response to antigenic peptides translated from different open reading frames", J. Immunol., 1998, vol. 161, pp. 3596-3606.

Wang et al., "Identification of TRP-2 as a human tumor antigen recognized by cytotoxic T lymphocytes", J. Exp. Med., 1996, vol. 184, pp. 2207-2216.

Wang et al., "Utilization of an alternative open reading frame of a normal gene in generating a novel human cancer antigen", J. Exp. Med., 1996, vol. 183, pp. 1131-1140.

Watt et al., "Comparison of ovine, bovine and porcine mucosal heparins and low molecular weight heparins by disaccharide analyses and 13C NMR", Carbohydrate Polymers, 1997, vol. 33, pp. 5-11.

Wölfel et al., "A p16INK4a-insensitive CDK4 mutant targeted by cytolytic T lymphocytes in a human melanoma", Science, 1995, vol. 269, pp. 1281-1284.

Wölfel et al., "Two tyrosinase nonapeptides recognized on HLA-A2 melanomas by autologous cytolytic T lymphocytes", Eur. J. Immunol., 1994, vol. 24, pp. 759-764.

Yates et al., "1H and 13C NMR spectral assignments of the major sequences of twelve systematically modified heparin derivatives", Carbohydrate Research, 1996, vol. 294, pp. 15-27.

Yoshida et al., "Analyisis of unsaturated disaccharides from glycosaminoglycuronan by high-performance liquid chromatography", Analytical Biochem., 1989, vol. 117, pp. 327-332.

Zorn et al., "A MAGE-6-encoded peptide is recognized by expanded lymphocytes infiltrating a spontaneously regressing human primary melanoma lesion", Eur. J. Immunol., 1999, vol. 29, pp. 602-607.

wherein R = SO$_3^-$ or H
and Y = SO$_3^-$ or Acetyl wherein R = SO$_3^-$ or H
and Y = SO$_3^-$ or Acetyl

EVALUATING HEPARIN PREPARATIONS

CLAIM OF PRIORITY

This application is a national stage application under 35 U.S.C. §371 of PCT Application No.: PCT/US2012/025920, filed Feb. 21, 2012, which claims priority to U.S. Application Ser. No. 61/444,985, filed on Feb. 21, 2011 and U.S. Application Ser. No. 61/559,228, filed on Nov. 14, 2011, the entire contents of which are hereby incorporated by reference.

BACKGROUND

Complex polysaccharides have been used as pharmaceutical interventions in a number of disease processes, including oncology, inflammatory diseases, and thrombosis. Examples of pharmaceutical interventions in this class are hyaluronic acid, an aid to wound healing and anti-cancer agent, and heparin, a potent anticoagulant and anti-thrombotic agent. Complex polysaccharides elicit their function primarily through binding soluble protein signaling molecules, including growth factors, cytokines and morphogens present at the cell surface and within the extracellular matrices between cells, as well as their cognate receptors present within this environment. In so doing, these complex polysaccharides effect critical changes in extracellular and intracellular signaling pathways important to cell and tissue function. For example, heparin binds to the coagulation inhibitor anti-thrombin III promoting its ability to inhibit factor IIa and Xa.

SUMMARY

In one aspect, the disclosure features a method of evaluating a heparin preparation (e.g., an unfractionated heparin preparation or a low molecular weight heparin (LMWH) preparation). The method includes:
  determining if one or more of the following structural signatures, is absent from, present in or present in an amount in a heparin preparation,

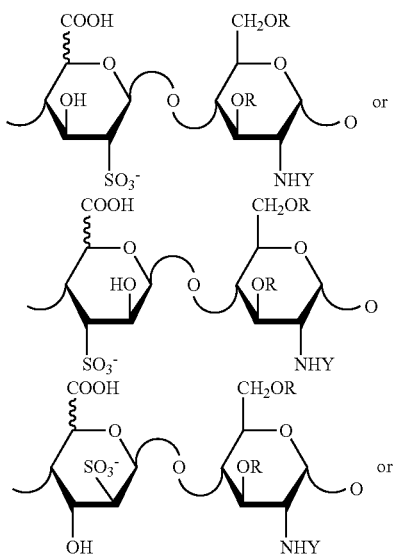

A

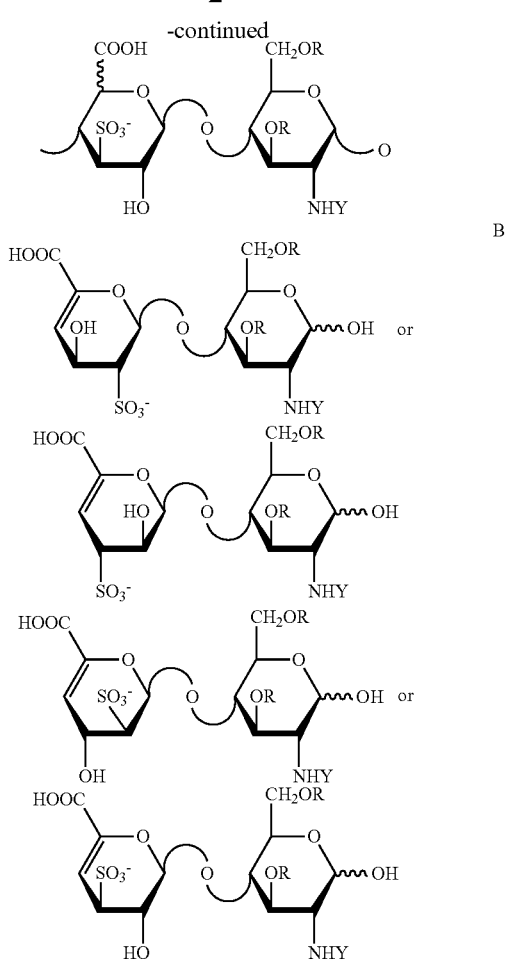

B wherein $R = SO_3^-$ or H and $Y = SO_3^-$ or Acetyl and
  making a decision or step regarding the heparin preparation, e.g., the heparin preparation is classified, selected, accepted or discarded, released or withheld, processed into a drug product, shipped, moved to a new location, formulated, labeled, packaged, released into commerce, sold, or offered for sale, if the structural signature is present or present in an amount, e.g., a statistically significant amount as compared to a reference standard.

In one embodiment, the structural signature is associated with peak X of FIG. 1.

In one embodiment, the presence of the structural signature or the presence in an amount, e.g., a statistically similar amount as compared to a reference standard, indicates that the heparin preparation was made by a method (e.g., a method that includes treatment with a base and/or an oxidation process, followed by treatment with a sulfite, e.g., sodium sulfite) and the absence of the structural signature, or an amount, e.g., an amount that is not statistically different in comparison to a reference standard, indicates that the heparin preparation was not made by the method (e.g., the method did not include treatment with a base and/or oxidation, followed by treatment with a sulfite, e.g., sodium sulfite).

In one embodiment, the method includes making a decision or step regarding the heparin preparation, e.g., the decision or step is to classify, select, accept, release, process into a drug product, ship, formulate, label, package, release into commerce, sell, or offer for sale, if the structural signature is present or present in an amount, e.g., an amount that is statistically different as compared to a reference standard.

In another embodiment, the method includes making a decision or step regarding the heparin preparation, e.g., the decision or step is to discard or withhold the heparin sample, if the structural signature is present or present in an amount that is statistically different, e.g., a statistically significant increase as compared to a reference standard.

In one embodiment, the method includes making a decision or step regarding the heparin preparation, e.g., the decision or step is to classify, select, accept, release, process into a drug product, ship, formulate, label, package, release into commerce, sell, or offer for sale, if the structural signature is not present or present in an amount, e.g., an amount that is not statistically different from a reference standard.

In another embodiment, the method includes making a decision or step regarding the heparin preparation, e.g., the decision or step is to discard or withhold the heparin sample, if the structural signature is not present or present in an amount, e.g., an amount that is not statistically different in comparison to a reference standard.

In one embodiment, the method can be used to determine suitability of the heparin preparation for use as a pharmaceutical or for use in making a pharmaceutical. In an embodiment, the heparin preparation is selected from the group of a starting material for the production of a drug, an intermediate in the production of a drug, a drug substance or a drug product.

In one embodiment, the heparin preparation is an unfractionated heparin preparation and the decision or step includes selecting the unfractionated heparin preparation for further processing, e.g., to produce a LMWH preparation, e.g., a LMWH preparation described herein. In one embodiment, the heparin preparation is selected for depolymerization, e.g., chemical and/or enzymatic depolymerization, and/or size fractionation to produce a LMWH preparation, e.g., a LMWH preparation described herein.

In one embodiment, the method further includes selecting the heparin preparation and processing the heparin preparation, e.g., to produce a drug product. In one embodiment, the heparin preparation is an unfractionated heparin preparation and the method further comprises depolymerizing the unfractionated heparin preparation, e.g., by chemical and/or enzymatic depolymerization, to produce a LMWH preparation, e.g., a LMWH preparation described herein. In one embodiment, the heparin preparation is an unfractionated heparin preparation and the method further comprises size fractionation of the unfractionated heparin preparation to produce a LMWH preparation, e.g., a LMWH preparation described herein. In one embodiment, the heparin preparation is an unfractionated heparin preparation and the method further comprises depolymerization and size fractionation of the unfractionated heparin preparation to produce a LMWH preparation, e.g., a LMWH preparation described herein. In one embodiment, the heparin preparation is an unfractionated heparin preparation and the method further comprises processing the unfractionated heparin preparation by one or more of the methods described herein.

In one embodiment, the heparin preparation is a commercially available unfractionated heparin preparation, e.g., a commercially available unfractionated heparin preparation described herein.

In one embodiment, the heparin preparation is a LMWH preparation and the decision or step is selecting, accepting, releasing, processing into a drug product, shipping, formulating, labeling, packaging, releasing into commerce, selling, or offering for sale the LMWH preparation.

In one embodiment, the LMWH preparation is a LMWH preparation described herein.

In an embodiment, the method further includes memorializing the decision or step taken.

In one embodiment, the presence or the amount of the structural signature indicates that the heparin preparation was made by a method that includes treatment with a base and/or an oxidation process followed by treatment with a sulfite, e.g., sodium sulfite. In one embodiment, the structural signature is present in an amount five-fold, ten-fold, fifteen-fold, twenty-fold, twenty five-fold, thirty-fold, thirty five-fold, forty-fold, forty-five fold or greater than the amount in a reference standard and it is determined that a method that includes base treatment and/or an oxidation process, followed by treatment with a sulfite, e.g., sodium sulfite, was used to make the heparin preparation.

In one embodiment, the absence, presence, or amount of the structural signature is determined using one or more methods such as high performance liquid chromatography (HPLC), nuclear magnetic resonance (NMR) (e.g., 1D-NMR or 2D-NMR), capillary electrophoresis (CE), mass spectrometry (e.g., matrix-assisted laser desorption ionization-mass spectrometry (MALDI-MS), electrospray ionization-mass spectrometry (ESI-MS), gel permeation-mass spectrometry (GPC-MS)), and fast protein liquid chromatography (FPLC).

In one aspect, the disclosure features a method of identifying if a process was used to make a heparin preparation (e.g., an unfractionated heparin preparation or a low molecular weight heparin (LMWH) preparation). The method includes:

determining if a structural signature described herein is absent from, present in or present in an amount, e.g., a statistically significant amount as compared to a reference standard, in a heparin preparation wherein the presence of the structural signature or the presence in an amount, e.g., an amount that is statistically different as compared to to a reference standard, indicates that the heparin preparation was made by a method (e.g., a method that includes base treatment, and/or an oxidation process, followed by treatment with a sulfite, e.g., sodium sulfite) and the absence of the structural signature, or an amount that is statistically similar as compared to a reference standard, indicates that the heparin preparation was not made by the method (e.g., the method did not include base treatment, and/or an oxidation process, followed by treatment with a sulfite, e.g., sodium sulfite); and making a decision or step regarding the heparin preparation, e.g., the heparin preparation is classified, selected, accepted or discarded, released or withheld, processed into a drug product, shipped, moved to a new location, formulated, labeled, packaged, released into commerce, sold, or offered for sale, if the heparin preparation was made by the method (e.g., the method includes treatment with a base and/or an oxidation process, followed by treatment with a sulfite, e.g., sodium sulfite) or if the heparin preparation was not made by the method (e.g., the method does not include treatment with a base and/or an oxidation, process followed by treatment with a sulfite, e.g., sodium sulfite).

In one embodiment, the method includes making a decision or step regarding the heparin preparation, e.g., the decision or step is to classify, select, accept, release, process into a drug product, ship, formulate, label, package, release into commerce, sell, or offer for sale, if the heparin preparation was not made by the method (e.g., the method did not include treatment with a base and/or an oxidation process, followed by treatment with a sulfite, e.g., sodium sulfite).

In another embodiment, the method includes making a decision or step regarding the heparin preparation, e.g., the decision or step is to discard or withhold the heparin sample, if the heparin preparation was made by the method (e.g., the method includes treatment with a base, and/or an oxidation process, followed by treatment with a sulfite, e.g., sodium sulfite).

In one embodiment, the method includes making a decision or step regarding the heparin preparation, e.g., the decision or step is to classify, select, accept, release, process into a drug product, ship, formulate, label, package, release into commerce, sell, or offer for sale, if the heparin preparation was made by the method (e.g., the method includes treatment with a base and/or an oxidation process, followed by treatment with a sulfite, e.g., sodium sulfite).

In another embodiment, the method includes making a decision or step regarding the heparin preparation, e.g., the decision or step is to discard or withhold the heparin sample, if the heparin preparation was not made by the method (e.g., the method does not include treatment with a base and/or an oxidation process, followed by treatment with a sulfite, e.g., sodium sulfite).

In one embodiment, the structural signature is a structural signature associated with peak X of FIG. 1.

In one embodiment, the method can be used to determine suitability of the heparin preparation for use as a pharmaceutical or for use in making a pharmaceutical. In an embodiment, the heparin preparation is selected from the group of a starting material for the production of a drug, an intermediate in the production of a drug, a drug substance or a drug product.

In one embodiment, the heparin preparation is an unfractionated heparin preparation and the decision or step includes selecting the unfractionated heparin preparation for further processing, e.g., to produce a LMWH preparation, e.g., a LMWH preparation described herein. In one embodiment, the heparin preparation is selected for depolymerization, e.g., chemical and/or enzymatic depolymerization, and/or size fractionation to produce a LMWH preparation, e.g., a LMWH preparation described herein.

In one embodiment, the method further includes selecting the heparin preparation and processing the heparin preparation, e.g., to produce a drug product. In one embodiment, the heparin preparation is an unfractionated heparin preparation and the method further comprises depolymerizing the unfractionated heparin preparation, e.g., by chemical and/or enzymatic depolymerization, to produce a LMWH preparation, e.g., a LMWH preparation described herein. In one embodiment, the heparin preparation is an unfractionated heparin preparation and the method further comprises size fractionation of the unfractionated heparin preparation to produce a LMWH preparation, e.g., a LMWH preparation described herein. In one embodiment, the heparin preparation is an unfractionated heparin preparation and the method further comprises depolymerization and size fractionation of the unfractionated heparin preparation to produce a LMWH preparation, e.g., a LMWH preparation described herein. In one embodiment, the heparin preparation is an unfractionated heparin preparation and the method further comprises processing the unfractionated heparin preparation by one or more of the methods described herein.

In one embodiment, the heparin preparation is a commercially available unfractionated heparin preparation, e.g., a commercially available unfractionated heparin preparation described herein.

In one embodiment, the heparin preparation is a LMWH preparation and the decision or step is selecting, accepting, releasing, processing into a drug product, shipping, formulating, labeling, packaging, releasing into commerce, selling, or offering for sale the LMWH preparation.

In one embodiment, the LMWH preparation is a LMWH preparation described herein.

In an embodiment, the method further includes memorializing the decision or step taken.

In one embodiment, if the structural signature is present, the method further comprises determining the amount of the structural signature present in the heparin preparation, and, e.g., comparing the amount to a reference standard.

In one embodiment, the absence or presence of the structural signature is determined.

In one embodiment, the presence or the amount of the structural signature indicates that the heparin preparation was made by a method that includes treatment with a base and/or an oxidation process, followed by treatment with a sulfite, e.g., sodium sulfite. In one embodiment, the structural signature is present in an amount five-fold, ten-fold, fifteen-fold, twenty-fold, twenty five-fold, thirty-fold, thirty five-fold, forty-fold, forty-five fold or greater than the amount in a reference standard and it is determined that a method that includes treatment with a base and/or an oxidation process, followed by treatment with a sulfite was used to make the heparin preparation.

In one embodiment, the absence, presence or amount of the structural signature is determined using one or more methods such as high performance liquid chromatography (HPLC), nuclear magnetic resonance (NMR) (e.g., 1D-NMR or 2D-NMR), capillary electrophoresis (CE), mass spectrometry (e.g., matrix-assisted laser desorption ionization-mass spectrometry (MALDI-MS), electrospray ionization-mass spectrometry (ESI-MS), gel permeation-mass spectrometry (GPC-MS)), and fast protein liquid chromatography (FPLC).

In another aspect, the disclosure features a method of identifying if a process was used to make a heparin preparation (e.g., an unfractionated heparin preparation or low molecular weight heparin (LMWH) preparation), comprising:

acquiring a value, e.g., obtained by a separation method, which indicates the absence, presence or amount of a structural signature described herein in a heparin preparation;

determining if the heparin preparation was made by a method (e.g., a method that includes treatment with a base and/or an oxidation process, of the heparin preparation followed by treatment with a sulfite, e.g., sodium sulfite), wherein the presence or amount of the structural signature, e.g., an amount that is statistically different as compared to a reference standard, indicates that the heparin preparation was made by the method (e.g., the method includes treatment with a base, and/or an oxidation process, followed by treatment with a sulfite, e.g., sodium sulfite) and the absence of the structural signature or the amount of the structural signature, e.g., the amount is not statistically different in comparison to a reference standard, indicates that the heparin preparation was not made by the method (e.g., the method did not include treatment with a base, and/or an oxidation process, followed by treatment with a sulfite, e.g., sodium sulfite); and making a decision or step regarding the heparin preparation, e.g., the heparin preparation is classified, selected, accepted or discarded, released or withheld, processed into a drug product, shipped, moved to a new location, formulated, labeled, packaged, released into commerce, sold, or offered for sale, if the heparin preparation was made by the method (e.g., the method includes treatment with a base, and/or an oxidation process, followed by treatment with a sulfite, e.g., sodium sulfite) or if the heparin preparation was not made by the method (e.g., the method does not include treatment with a base, and/or an oxidation process, followed by treatment with a sulfite, e.g., sodium sulfite), In one embodiment, the method includes making a decision or step regarding the heparin preparation, e.g., the decision or step is to classify, select, accept, release, process into a drug product, ship, formulate, label, package, release into commerce, sell, or offer for sale, if the heparin preparation was not made by the method (e.g., the method does not include treatment with a base, and/or an oxidation process, followed by treatment with a sulfite, e.g., sodium sulfite).

In another embodiment, the method includes making a decision or step regarding the heparin preparation, e.g., decision or step is to discard or withhold the heparin preparation, if the heparin preparation was made by the method (e.g., the method includes treatment with a base, and/or an oxidation, followed by treatment with a sulfite, e.g., sodium sulfite).

In one embodiment, the method includes making a decision or step regarding the heparin preparation, e.g., the decision or step is to classify, select, accept, release, process into a drug product, ship, formulate, label, package, release into commerce, sell, or offer for sale, if the heparin preparation was made by the method (e.g., the method includes treatment with a base, and/or an oxidation process, followed by treatment with a sulfite, e.g., sodium sulfite).

In another embodiment, the method includes making a decision or step regarding the heparin preparation, e.g., decision or step is to discard or withhold the heparin preparation, if the heparin preparation was not made by the method (e.g., the method does not include treatment with a base, and/or an oxidation process, followed by treatment with a sulfite, e.g., sodium sulfite).

In one embodiment, the method can be used to determine suitability of the heparin preparation for use as a pharmaceutical or for use in making a pharmaceutical. In an embodiment, the heparin preparation is selected from the group of a starting material for the production of a drug, an intermediate in the production of a drug, a drug substance or a drug product.

In one embodiment, the heparin preparation is an unfractionated heparin preparation and the decision or step includes selecting the unfractionated heparin preparation for further processing, e.g., to produce a LMWH preparation, e.g., a LMWH preparation described herein. In one embodiment, the heparin preparation is selected for depolymerization, e.g., chemical and/or enzymatic depolymerization, and/or size fractionation to produce a LMWH preparation, e.g., a LMWH preparation described herein.

In one embodiment, the method further includes selecting the heparin preparation and processing the heparin preparation, e.g., to produce a drug product, e.g., by one or more of the methods described herein.

In one embodiment, the heparin preparation is a commercially available unfractionated heparin preparation, e.g., a commercially available unfractionated heparin preparation described herein.

In one embodiment, the heparin preparation is a LMWH preparation and the decision or step is selecting, accepting, releasing, processing into a drug product, shipping, formulating, labeling, packaging, releasing into commerce, selling, or offering for sale the LMWH preparation.

In one embodiment, the LMWH preparation is a LMWH preparation described herein.

In an embodiment, the method further includes memorializing the decision or step taken.

In one embodiment, if the structural signature is present, the method comprises determining the amount of the structural signature present in the heparin preparation.

In one embodiment, the evaluation indicates the absence or presence of the structural signature.

In one embodiment, the presence or amount of the structural signature (e.g., an amount that is statistically different in comparison to a reference standard) indicates that the heparin preparation was made by a method that includes treatment with a base and/or an oxidation process, followed by treatment with a sulfite, e.g., sodium sulfite. In one embodiment, the structural signature is present in an amount five-fold, ten-fold, fifteen-fold, twenty-fold, twenty five-fold, thirty-fold, thirty five-fold, forty-fold, forty-five fold or greater than the amount in a reference standard and it is determined that a method that includes treatment with a base, and/or an oxidation process, followed by treatment with a sulfite, e.g., sodium sulfite, was used to make the heparin preparation.

In one embodiment, the separation method is one or more separation method described herein.

In another aspect, the disclosure features a method of identifying if a process was used to make a heparin preparation (e.g., an unfractionated heparin preparation or low molecular weight heparin (LMWH) preparation), comprising:
    using a separation method to determine the absence, presence or amount of a structural signature described herein in a heparin preparation; and
    determining if the heparin preparation was made by a method (e.g., a method that includes treatment with a base and/or an oxidation process, of the heparin preparation followed by treatment with a sulfite, e.g., sodium sulfite), wherein the presence or amount of the structural signature, e.g., an amount that is statistically different as compared to a reference standard, indicates that the heparin preparation was made by the method (e.g., the method includes treatment with a base, and/or an oxidation process, of the heparin preparation followed by treatment with a sulfite, e.g., sodium sulfite) and the absence or amount of the structural signature, e.g., an amount that is not statistically different as compared to a reference standard, indicates that the heparin preparation was not made by the method (e.g., the method did not include treatment with a base, and/or an oxidation process, of the heparin preparation followed by treatment of the heparin preparation with a sulfite, e.g., sodium sulfite).

In an embodiment, the method further includes making a decision or step regarding the heparin preparation, e.g., the heparin preparation is classified, selected, accepted or discarded, released or withheld, processed into a drug product, shipped, moved to a new location, formulated, labeled, packaged, released into commerce, sold, or offered for sale, if the heparin preparation was made by the method (e.g., the method includes treatment with a base, and/or an oxidation process, followed by treatment with a sulfite, e.g., sodium sulfite) or if the heparin preparation was not made by the method (e.g., the method does not include treatment with a base, and/or an oxidation process, followed by treatment with a sulfite, e.g., sodium sulfite).

In one embodiment, the method can be used to determine suitability of the heparin preparation for use as a pharmaceutical or for use in making a pharmaceutical. In an embodiment, the heparin preparation is selected from the group of a starting material for the production of a drug, an intermediate in the production of a drug, a drug substance or a drug product.

In one embodiment, the heparin preparation is an unfractionated heparin preparation and the method further includes selecting the unfractionated heparin preparation for further processing, e.g., to produce a LMWH preparation, e.g., a LMWH preparation described herein. In one embodiment, the heparin preparation is selected for depolymerization, e.g., chemical and/or enzymatic depolymerization, and/or size fractionation to produce a LMWH preparation, e.g., a LMWH preparation described herein.

In one embodiment, the method further includes selecting the heparin preparation and processing the heparin preparation, e.g., to produce a drug product, e.g., by one or more of the methods described herein.

In one embodiment, the structural signature is a structural signature associated with peak X of FIG. 1.

In one embodiment, the heparin preparation is a commercially available unfractionated heparin preparation, e.g., a commercially available unfractionated heparin preparation described herein.

In one embodiment, the heparin preparation is a LMWH preparation and the method further includes making a decision or a step. For example, the decision or step can be selecting, accepting, releasing, processing into a drug product, shipping, formulating, labeling, packaging, releasing into commerce, selling, or offering for sale the LMWH preparation. In an embodiment, the method further includes memorializing the decision or step taken.

In one embodiment, the LMWH preparation is a LMWH preparation described herein.

In one embodiment, if the structural signature is present, the method further comprises determining the amount of the structural signature present in the heparin preparation.

In one embodiment, the absence or presence of the structural signature is determined.

In one embodiment, the presence or amount of the structural signature, e.g., an amount that is statistically different in comparison to a reference standard, indicates that the heparin preparation was made by a method that includes treatment with a base and/or an oxidation process followed by treatment with a sulfite, e.g., sodium sulfite. In one embodiment, the presence or amount of the structural signature, e.g., an amount that is statistically different in comparison to a reference standard, indicates that the heparin preparation was made by a method that includes treatment with a base, and/or an oxidation process, followed by treatment with a sulfite, e.g., sodium sulfite. In one embodiment, the structural signature is present in an amount five-fold, ten-fold, fifteen-fold, twenty-fold, twenty five-fold, thirty-fold, thirty five-fold, forty-fold, forty-five fold or greater than the amount in a reference standard and it is determined that a method that includes treatment with a base, and/or an oxidation process, followed by treatment with a sulfite, e.g., sodium sulfite, was used to make the heparin preparation.

In one embodiment, the absence, presence or amount of the structural signature is determined using one or more separation method described herein.

In one aspect, the disclosure features a method of identifying if a process was used to make a heparin preparation (e.g., an unfractionated heparin preparation or a low molecular weight heparin (LMWH) preparation). The method includes:

determining an amount of sulfation of a disaccharide present in polymers of a heparin preparation wherein the amount of sulfation, e.g., an amount that differs statistically significantly in comparison to a reference standard, indicates that the heparin preparation was made by a method (e.g., a method that includes treatment with a base, and/or an oxidation process, followed by treatment with a sulfite, e.g., sodium sulfite) and an amount that does not differ statistically significantly in comparison to a reference standard, indicates that the heparin preparation was not made by the method (e.g., the method did not include treatment with a base, and/or an oxidation process, followed by treatment with a sulfite, e.g., sodium sulfite); and making a decision or step regarding the heparin preparation, e.g., the heparin preparation is classified, selected, accepted or discarded, released or withheld, processed into a drug product, shipped, moved to a new location, formulated, labeled, packaged, released into commerce, sold, or offered for sale, if the heparin preparation was made by the method (e.g., the method includes treatment with a base, and/or an oxidation process, followed by treatment with a sulfite, e.g., sodium sulfite) or if the heparin preparation was not made by the method (e.g., the method does not include treatment with a base, e.g., oxidation, followed by treatment with a sulfite, e.g., sodium sulfite).

In one embodiment, the method includes making a decision or step regarding the heparin preparation, e.g., the decision or step is to classify, select, accept, release, process into a drug product, ship, formulate, label, package, release into commerce, sell, or offer for sale, if the heparin preparation was not made by the method (e.g., the method did not include treatment with a base, and/or an oxidation process, followed by treatment with a sulfite, e.g., sodium sulfite).

In another embodiment, the method includes making a decision or step regarding the heparin preparation, e.g., the decision or step is to discard or withhold the heparin sample, if the heparin preparation was made by the method (e.g., the method includes treatment with a base, and/or an oxidation process, followed by treatment with a sulfite, e.g., sodium sulfite).

In one embodiment, the method includes making a decision or step regarding the heparin preparation, e.g., the decision or step is to classify, select, accept, release, process into a drug product, ship, formulate, label, package, release into commerce, sell, or offer for sale, if the heparin preparation was made by the method (e.g., the method did includes treatment with a base, and/or an oxidation process, followed by treatment with a sulfite, e.g., sodium sulfite).

In another embodiment, the method includes making a decision or step regarding the heparin preparation, e.g., the decision or step is to discard or withhold the heparin sample, if the heparin preparation was not made by the method (e.g., the method did not include treatment with a base, and/or an oxidation process, followed by treatment with a sulfite, e.g., sodium sulfite).

In one embodiment, the method can be used to determine suitability of the heparin preparation for use as a pharmaceutical or for use in making a pharmaceutical. In an embodiment, the heparin preparation is selected from the group of a starting material for the production of a drug, an intermediate in the production of a drug, a drug substance or a drug product.

In one embodiment, the heparin preparation is an unfractionated heparin preparation and the decision or step includes selecting the unfractionated heparin preparation for further processing, e.g., to produce a LMWH preparation, e.g., a LMWH preparation described herein. In one embodiment, the heparin preparation is selected for depolymerization, e.g., chemical and/or enzymatic depolymerization, and/or size fractionation to produce a LMWH preparation, e.g., a LMWH preparation described herein.

In one embodiment, the method further includes selecting the heparin preparation and processing the heparin preparation, e.g., to produce a drug product. In one embodiment, the heparin preparation is an unfractionated heparin preparation and the method further comprises depolymerizing the unfractionated heparin preparation, e.g., by chemical and/or enzymatic depolymerization, to produce a LMWH preparation, e.g., a LMWH preparation described herein. In one embodiment, the heparin preparation is an unfractionated heparin preparation and the method further comprises size fractionation of the unfractionated heparin preparation to produce a LMWH preparation, e.g., a LMWH preparation described herein. In one embodiment, the heparin preparation is an unfractionated heparin preparation and the method further comprises depolymerization and size fractionation of the unfractionated heparin preparation to produce a LMWH preparation, e.g., a LMWH preparation described herein. In one embodiment, the heparin preparation is an unfractionated heparin preparation and the method further comprises processing the unfractionated heparin preparation by one or more of the methods described herein.

In one embodiment, the heparin preparation is a commercially available unfractionated heparin preparation, e.g., a commercially available unfractionated heparin preparation described herein.

In one embodiment, the heparin preparation is a LMWH preparation and the decision or step is selecting, accepting, releasing, processing into a drug product, shipping, formulating, labeling, packaging, releasing into commerce, selling, or offering for sale the LMWH preparation.

In one embodiment, the LMWH preparation is a LMWH preparation described herein.

In an embodiment, the method further includes memorializing the decision or step taken.

In one embodiment, the method further comprises determining if a structural signature is present in the heparin preparation, and, e.g., comparing the amount to a reference standard.

In one embodiment, the presence or the amount of the structural signature, e.g., an amount that differs statistically significantly in comparison to a reference standard, indicates that the heparin preparation was made by a method that includes treatment with a base, and/or an oxidation process followed by treatment with a sulfite, e.g., sodium sulfite.

In one embodiment, the amount of structural signature is determined using one or more methods such as high performance liquid chromatography (HPLC), nuclear magnetic resonance (NMR) (e.g., 1D-NMR or 2D-NMR), capillary electrophoresis (CE), mass spectrometry (e.g., matrix-assisted laser desorption ionization-mass spectrometry (MALDI-MS), electrospray ionization-mass spectrometry (ESI-MS), gel permeation-mass spectrometry (GPC-MS)), and fast protein liquid chromatography (FPLC).

In an embodiment, the method further includes making a decision or step regarding the heparin preparation, e.g., the heparin preparation is classified, selected, accepted or discarded, released or withheld, processed into a drug product, shipped, moved to a new location, formulated, labeled, packaged, released into commerce, sold, or offered for sale, if the heparin preparation was made by the method (e.g., the method includes treatment with a base, and/or an oxidation process, followed by treatment with a sulfite, e.g., sodium sulfite) or if the heparin preparation was not made by the method (e.g., the method does not include treatment with a base, e.g., oxidation followed by treatment with a sulfite, e.g., sodium sulfite).

In one embodiment, the method can be used to determine suitability of the heparin preparation for use as a pharmaceutical or for use in making a pharmaceutical. In an embodiment, the heparin preparation is selected from the group of a starting material for the production of a drug, an intermediate in the production of a drug, a drug substance or a drug product.

In one embodiment, the heparin preparation is an unfractionated heparin preparation and the method further includes selecting the unfractionated heparin preparation for further processing, e.g., to produce a LMWH preparation, e.g., a LMWH preparation described herein. In one embodiment, the heparin preparation is selected for depolymerization, e.g., chemical and/or enzymatic depolymerization, and/or size fractionation to produce a LMWH preparation, e.g., a LMWH preparation described herein.

In one embodiment, the method further includes selecting the heparin preparation and processing the heparin preparation, e.g., to produce a drug product, e.g., by one or more of the methods described herein.

In one embodiment, the heparin preparation is a commercially available unfractionated heparin preparation, e.g., a commercially available unfractionated heparin preparation described herein.

In one embodiment, the heparin preparation is a LMWH preparation and the method further includes making a decision or a step. For example, the decision or step can be selecting, accepting, releasing, processing into a drug product, shipping, formulating, labeling, packaging, releasing into commerce, selling, or offering for sale the LMWH preparation. In an embodiment, the method further includes memorializing the decision or step taken.

In one embodiment, the LMWH preparation is a LMWH preparation described herein.

In one embodiment, the method further comprises determining the amount of a structural signature is present or present in an amount in the heparin preparation.

In one embodiment, the structural signature associated with peak X of FIG. 1 is determined.

In one embodiment, the presence or amount of the structural signature, e.g., an amount that differs statistically significantly in comparison to a reference standard, indicates that the heparin preparation was made by a method that includes treatment with a base, and/or an oxidation process, followed by treatment with a sulfite, e.g., sodium sulfite. In one embodiment, the presence or amount of the structural signature, e.g., an amount that differs statistically significantly in comparison to a reference standard, indicates that the heparin preparation was made by a method that includes treatment with a base, and/or an oxidation process, and treatment with a sulfite, e.g., sodium sulfite. In one embodiment, the structural signature is present in an amount five-fold, ten-fold, fifteen-fold, twenty-fold, twenty five-fold, thirty-fold, thirty five-fold, forty-fold, forty-five fold or greater than the amount in a reference standard and it is determined that a method that includes treatment with a base, and/or an oxidation process, followed by treatment with a sulfite, e.g., sodium sulfite, was used to make the heparin preparation.

In one embodiment, the amount of monosulfation, disulfation and/or trisulfation is determined using one or more separation method described herein.

In another aspect, the disclosure features a method of identifying a structural signature that is indicative of a method used to make a heparin preparation (e.g., an unfractionated heparin preparation or low molecular weight heparin (LMWH) preparation), comprising:
    providing (e.g., acquiring) an evaluation of a structural signature or signatures of a first heparin preparation made by a first method;
    providing (e.g., acquiring) an evaluation of a structural signature or signatures of a second heparin preparation made by a second method that differs from the first method;
    identifying the at least one structural signature of the first heparin preparation that is present in the first heparin preparation and absent or present in a different amount in the second heparin preparation; and
    identifying the at least one structural signature of the first heparin preparation identified in the previous step or the amount of the at least one structural signature of the first heparin preparation identified in the previous step as a reference standard for identifying a heparin preparation made by the first method.

In one embodiment, the reference standard is memorialized, e.g., in print or in a computer readable record.

In one embodiment, the evaluation was obtained using a separation method, e.g., a separation method described herein.

In one embodiment, the heparin preparation is a commercially available unfractionated heparin preparation, e.g., a commercially available unfractionated heparin preparation described herein. In an embodiment, the heparin preparation is a LMWH preparation, e.g., a LMWH preparation described herein.

In one aspect, the disclosure features a method of analyzing a heparin preparation (e.g., an unfractionated heparin preparation or low molecular weight heparin (LMWH) preparation), comprising:
    providing (e.g., acquiring) a value indicative of the absence, presence or amount of a structural signature or signatures of a heparin preparation, and
    comparing the value to a reference standard, e.g., a reference standard identified by a method described herein, to determine if the heparin preparation has a structural signature that identifies the method used to make the heparin sample, wherein the presence of the structural signature indicates that the heparin sample was made by a method and the absence of the structural signature indicates that that the heparin sample was not made by the method; and
    optionally, making a decision or step regarding the heparin sample, e.g., the heparin sample is classified, selected, accepted or discarded, released or withheld, processed into a drug product, shipped, moved to a new location, formulated, labeled, packaged, released into commerce, sold, or offered for sale, if the heparin sample was not made by the method.

In one embodiment, the decision or step is memorialized.

In one embodiment, the structural signature is determined using a separation method, e.g., a separation method described herein.

In one embodiment, the heparin preparation is a commercially available unfractionated heparin preparation, e.g., a commercially available unfractionated heparin preparation described herein. In an embodiment, the heparin preparation is a LMWH preparation, e.g., a LMWH preparation described herein.

In one aspect, the disclosure features a database that correlates the presence or amount of a structural signature, with a method used to make the heparin preparation (e.g., a method that includes oxidation and/or treatment with a sulfite).

The details of one or more embodiments are set forth in the accompanying figures and the description below. Other features, objects, and advantages of the invention will be apparent from the description and figures, and from the claims.

BRIEF DESCRIPTION OF THE FIGURES

The figures are first briefly described.

DETAILED DESCRIPTION

The disclosure is based on the finding that characteristic structural signatures within a heparin preparation reflect the process used to make the heparin preparation. The structural signatures that reflect the process used to make the heparin preparation are one or more of the following:

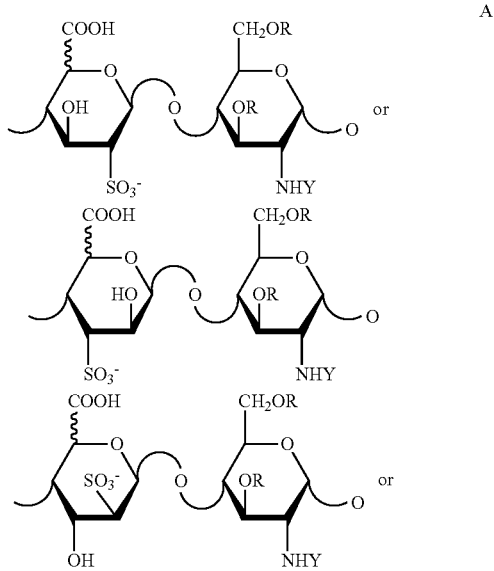

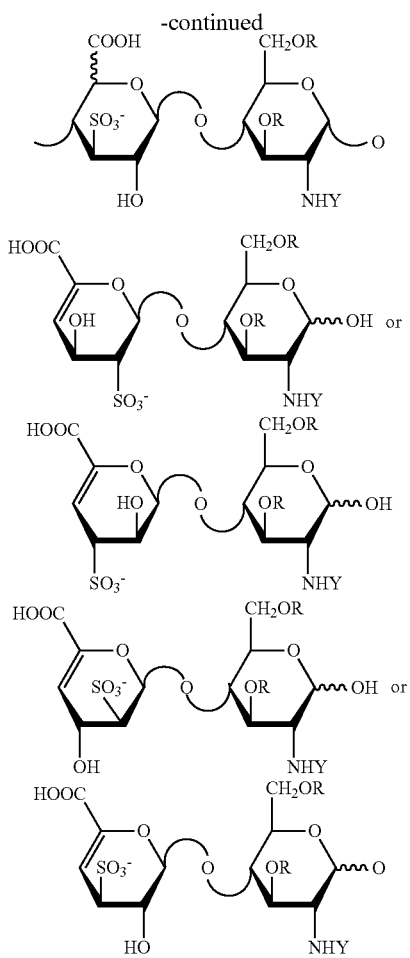

wherein R = SO$_3^-$ or H and Y = SO$_3^-$ or Acetyl

Figure 1:
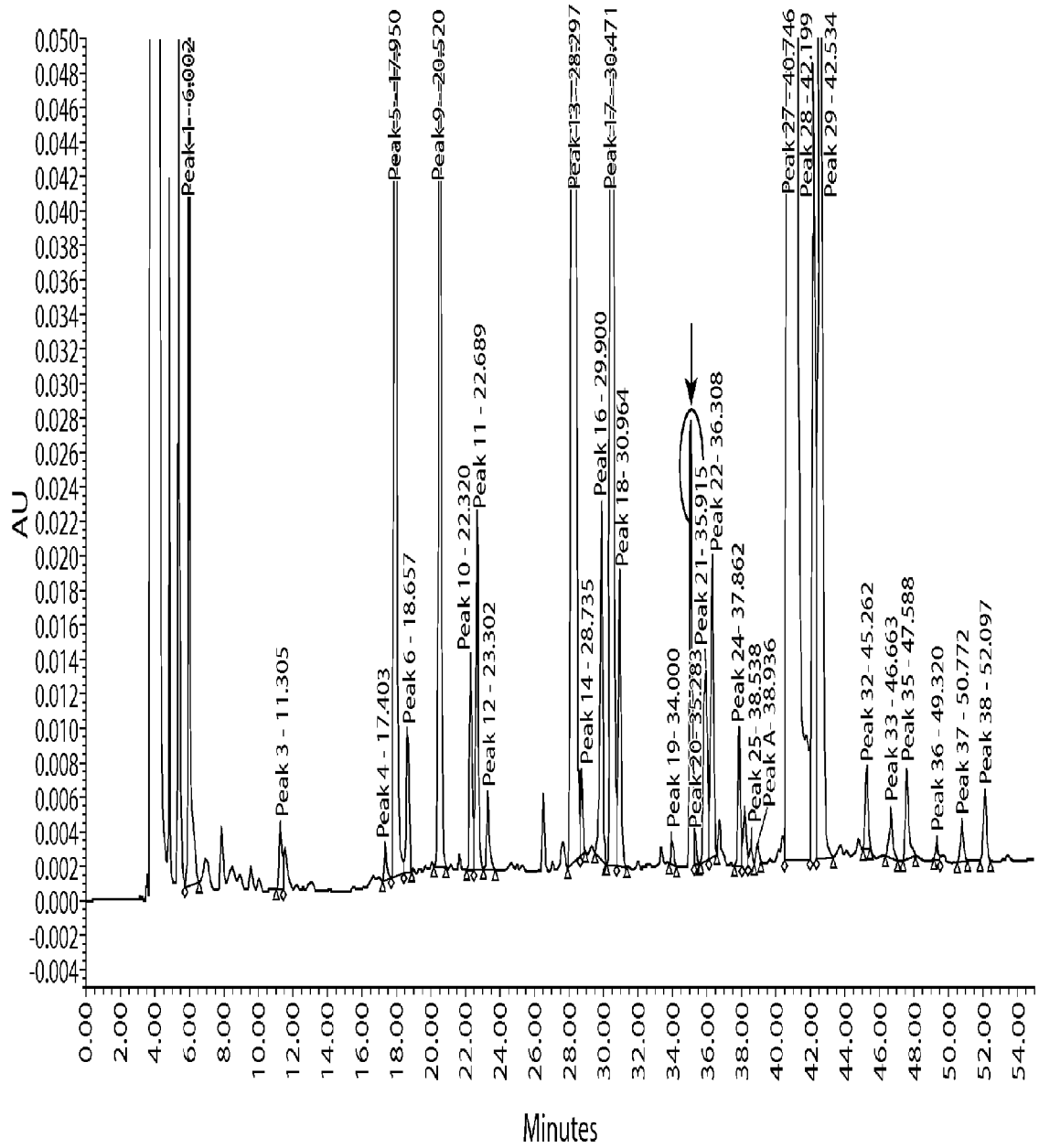
FIG. 1 depicts an HPLC chromatograph. Peak X (i.e. the peak eluting at ~34-35 minutes in the chromatogram) is indicated by the arrow.
Figure 2A:
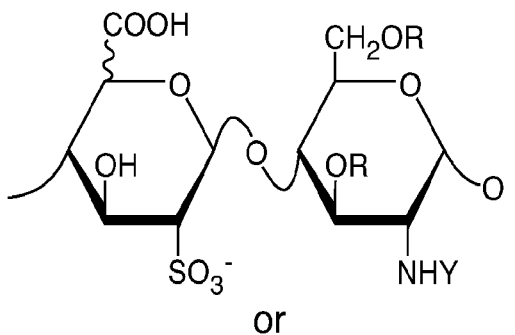
FIG. 2A depicts the potential structures that could be generated when a sample of unfractionated heparin is treated with base, and/or an oxidation process e.g. hydrogen peroxide treatment, followed by subsequent treatment with a sulfite salt (like sodium sulfite). The structure/s formed can be present within a chain of unfractionated heparin, at its non-reducing end, or its reducing end. Following enzymatic digestion of the UFH to its constituent building blocks, these structures could form disaccharides as shown in FIG. 2B, or could also be present as longer fragments like tetrasaccharides in the digest of UFH. These structures would be observed in the Composition Analysis by IPRP-HPLC assay e.g. peak X in the HPLC chromatogram of FIG. 1.
Figure 2A:
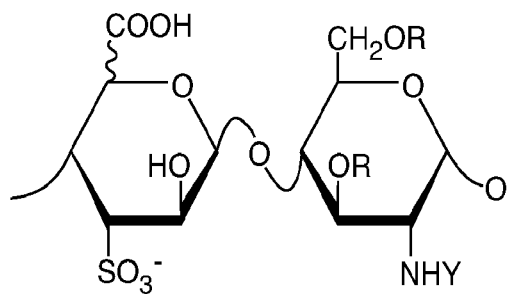
Figure 2A:
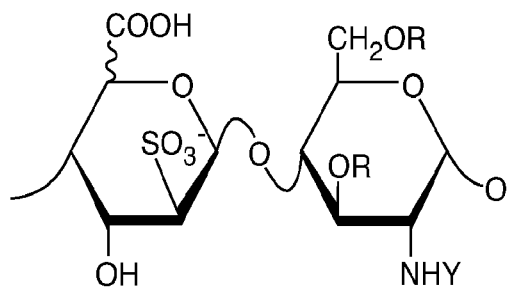
Figure 2A:
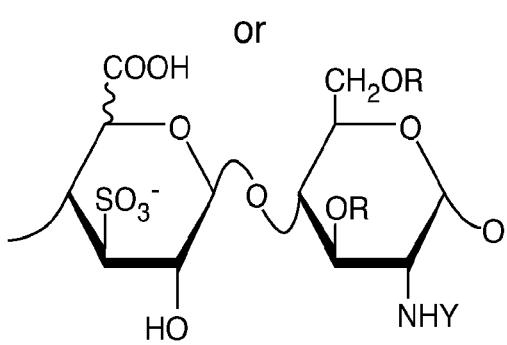
Figure 2B:
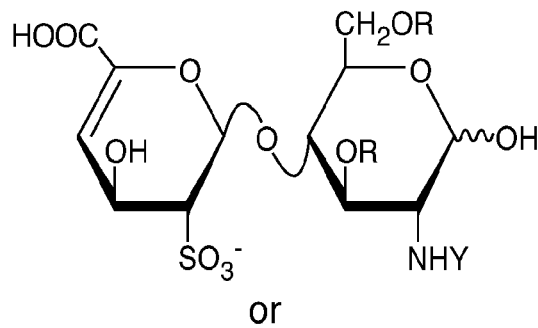
Figure 2B:
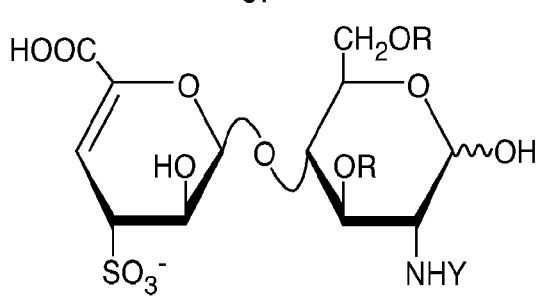
Figure 2B:
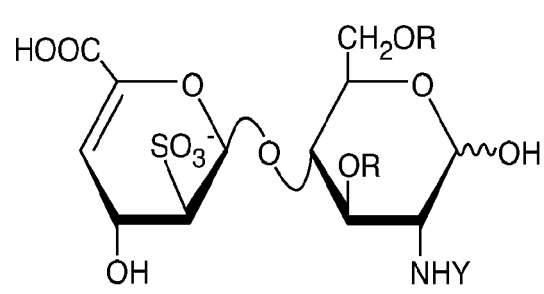
Figure 2B:
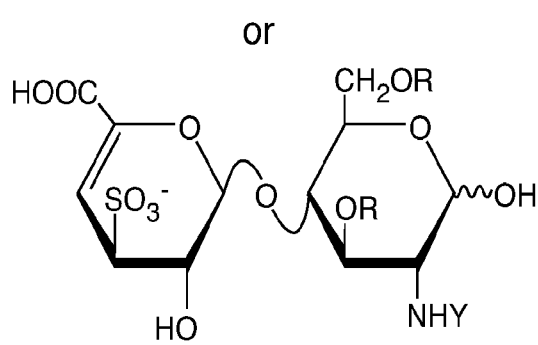
Figure 3:
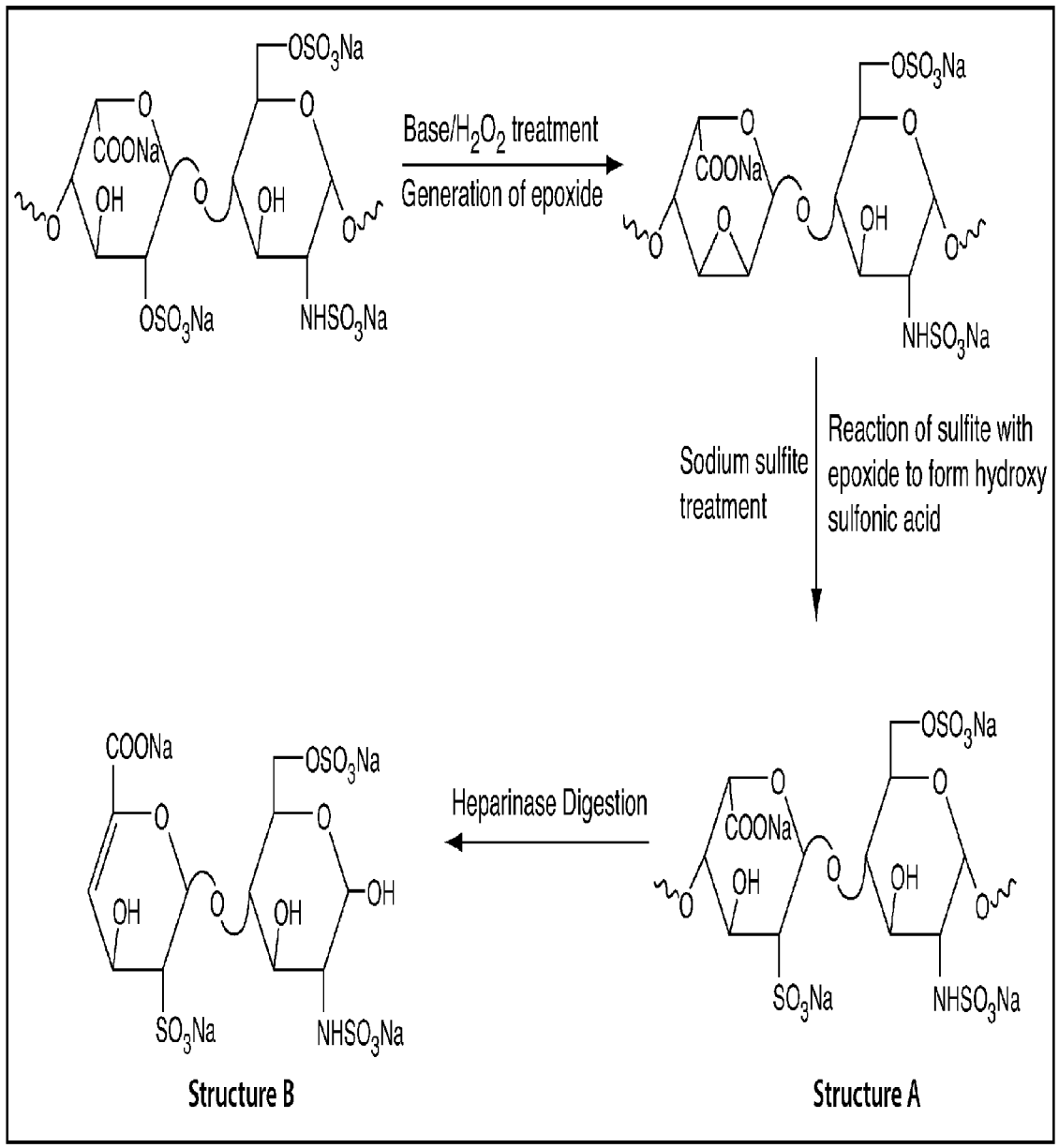
FIG. 3 depicts a mechanism of action which leads to the formation of the structures shown in FIG. 2. Structure A represents the structure as present within an oligosaccharide chain or chain of heparin. Structure B represents the disaccharide structure generated after exhaustive enzymatic digestion of heparin for compositional analysis.

The presence, absence, and/or amount of one or more structural signatures in a heparin preparation can be identified by the appearance of peak X of FIG. 1. For example, the presence of a structural signature or the amount of a structural signature in an unfractionated heparin represents a characteristic structural signature that is reflective of a processing step that includes treatment with a base, and/or an oxidation process, followed by treatment with a sulfite, e.g., sodium sulfite, in the manufacture of unfractionated heparin. Therefore, in some embodiments, a method described herein can include evaluating the absence, presence or amount of a structural signature. "Presence" means whether a structural signature can be detected. "Amount" refers to the amount, e.g., as % by weight or number (i.e. moles).

As used herein, "acquiring a value" refers to any process that results in possession of the value. In an embodiment, acquiring a value comprises subjecting a sample to a process which results in a physical change in the sample or another substance, e.g., an analytical reagent or a device used in the analysis. Such methods comprise analytical methods, e.g., a method which include one or more of the following: separating a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non covalent bond, between a first and a second atom of the analyte.

Typical analytical methods include high performance liquid chromatography (HPLC), nuclear magnetic resonance (NMR), capillary electrophoresis (CE) and mass spectrometry (e.g., matrix-assisted laser desorption ionization-mass spectrometry (MALDI-MS), electrospray ionization-mass spectrometry (ESI-MS), gel permeation-mass spectrometry (GPC-MS)), and fast protein liquid chromatography (FPLC).

In an embodiment, a party that practices the method performs the process. As used herein, "directly acquiring," refers to a process in which the party that practices the method performs the process. In an embodiment, a party that practices the method receives the value from another party. As used herein, "indirectly acquiring," refers to a process in which the party that practices the method receives the value from another party. Typically, even in embodiments characterized by indirect acquisition, some party has subjected a sample to a process as described above that results in a physical change in the sample or another substance. In an embodiment, a party that practices the method of evaluating instructs another party to perform the process, and e.g., a party that practices the method receives the value.

Heparin Preparations

A heparin preparation, as used herein, is a preparation which contains heparin or a preparation derived there from, and thus includes unfractionated heparin, low molecular weight heparin (LMWH), ultra low molecular weight heparin (ULMWH) and the like.

The term "unfractionated heparin (UFH)" as used herein, is heparin purified from porcine intestinal mucosa. UFH can be used, e.g., as a starting material in the process to form a LMWH. Unfractionated heparin is commercially available from several vendors including Abbott, Organon, Riker, Invenex, Baxter, Calbiochem, Sigma, Changzhou Qianhong CQ Biopharma, Nanjing King Friend or Upjohn. In some embodiments, the heparin is made by a process that includes treatment with a base and/or an oxidation step. The oxidation step can include using at least one of: a permanganate salt, peroxide, periodate, chlorine, chlorine dioxide, perchlorate, peracetic acid, and combinations thereof. Preferably, the oxidation step includes using a permanganate salt, e.g., potassium permanganate, sodium permanganate, or quaternary ammonium permanganate. Alternatively, in a preferred embodiment, the oxidation step includes a peroxide, preferably hydrogen peroxide. In some embodiments, the heparin is made by a process that includes treatment with a sulfite, e.g., Na$_2$SO$_3$.

The heparin preparation can also be a LMWH preparation. Examples of LMWH preparations include, but are not limited to, an enoxaparin preparation (Lovenox™ or Clexane™); a dalteparin preparation (Fragmin™); a certoparin preparation (Sandoparin™ or Embollex); an ardeparin preparation (Normiflo™); a nadroparin preparation (Fraxiparin™); a parnaparin preparation (Fluxum™); a reviparin preparation (Clivarin™); a tinzaparin preparation (Innohep™ or Logiparin™), a fondaparinux preparation (Arixtra™), or a M118-REH preparation. In some embodiments, the LWMH preparation can be a LMWH preparation made by one or more of the following methods: fractionation using solvents (French Patent No.: 2,440,376, U.S. Pat. No. 4,692,435); fractionation using an anionic resin (French Patent No.: 2,453,875); gel filtration (Barrowcliffe (1977) Thromb. Res. 12:27-36); affinity chromatography (U.S. Pat. No. 4,401,758); controlled depolymerization by means of a chemical agent including, but not limited to, nitrous acid (European Patent No.: 014 184 B1, European Patent No.: 037 319 B1, European Patent No.: 076 279 B1, European Patent No.: 623 629 B1, French Patent No.: 2,503,714, U.S. Pat. No.

4,804,652 and PCT Publication No.: WO 81/03276), beta-elimination from a heparin ester (European Patent No.: 040 144 B1, U.S. Pat. No. 5,389,618), periodate (EP 287477), sodium borohydride (EP 347588, EP 380943), ascorbic acid (U.S. Pat. No. 4,533,549), hydrogen peroxide (U.S. Pat. No. 4,629,699, U.S. Pat. No. 4,791,195), quaternary ammonium hydroxide from a quaternary ammonium salt of heparin (U.S. Pat. No. 4,981,955), alkali metal hydroxide (European Patent No.: 380 943, European Patent No.: 347 588), by an enzymatic route (European Patent No.: 064 452, U.S. Pat. No. 4,396,762, European Patent No.: 244 235, European Patent No.: 244 236; U.S. Pat. No. 4,826,827; U.S. Pat. No. 3,766,167), by means of irradiation (European Patent No.: 269 981), and other methods or combinations of methods such as those described in U.S. Pat. No. 4,303,651, U.S. Pat. No. 4,757,057, U.S. Publication No.: 2007/287683, PCT Publication No.: WO 2009/059284 and PCT Publication No.: WO 2009/059283.

In some embodiments, a heparin preparation, e.g., an unfractionated heparin preparation, can be selected for further processing based upon the absence, presence or amount of a structural signature that indicates the method used to make the heparin preparation. For example, an unfractionated heparin preparation can be selected for further processing, e.g., into a LMWH preparation. The unfractionated heparin preparation can be selected for further processing, e.g., by one or more of the methods described above.

Database

The disclosure also features a database that correlates the presence or amount of a structural signature, with a method used to make the heparin preparation (e.g., a method that includes treatment with a base, and/or an oxidation process, followed by treatment with a sulfite, e.g., sodium sulfite), and use of such a database, e.g., in a method described herein. The term "database" refers to a collection of data. Typically, it is organized so that its contents can easily be accessed, managed, and updated. In one embodiment, the database is configured or managed to ensure its integrity and quality, to minimize content beyond records described herein, and to allow controlled access. The database is presented or memorialized on a medium. The medium can be, e.g., a traditional paper medium or other medium which displays printed or written symbols which can be directly (e.g., without the aid of a computer) used by a human being. Such a database can exist as a set of printed tables, or a card catalogue, which, e.g., show the relationship of the structural signature to the method used to produce the heparin preparation. The database can also be presented or memorialized in electronic or other computer readable form. These embodiments can range from simple spreadsheets to more complex embodiments. The database need not be deposited on a single unit of medium, e.g., in a single table or book, or on a single computer or network. A database, e.g., can combine a traditional medium as described above with a computer-readable medium. Typically, the database will contain a collection of records, wherein each record relates a structural signature to a method of manufacture by way of a correlative function. The database can be organized in a number of ways, e.g., as a relational database. Typically the database is in a format that can be searched for specific information or records by techniques specific to each database. A computer database is typically a structured collection of records stored in a computer or computers so that a program can consult it to answer queries.

Reference Values and Standards

A reference standard, by way of example, can be a value determined from a reference heparin preparation (e.g., a commercially available heparin preparation or a heparin preparation made by a particular method). For example, a reference standard can be a value for the presence of a structural signature in a preparation, e.g., a reference heparin preparation. The reference standard can be numerical or non-numerical, e.g., it can be a qualitative value, e.g., yes or no, or present or not present at a preselected level of detection, or graphic or pictorial. The reference standard can also be values for the presence of more than one structural signature in a sample. For example, the reference standard can be a map of a signature structure present in a heparin preparation when analyzed by a separation method described herein. The reference standard can also be a release standard (a release standard is a standard which should be met to allow commercial sale of a product) or production standard, e.g., a standard which is imposed, e.g., by a party, e.g., the FDA, on a heparin or LMWH.

Detection of Structural Signatures

The absence, presence or amount of a structural signature can be determined by any separation method that allows for identification of the structural signature in a heparin preparation. For example, one or more of the following methods can be used: high performance liquid chromatography (HPLC), nuclear magnetic resonance (NMR), capillary electrophoresis (CE) and mass spectrometry (e.g., matrix-assisted laser desorption ionization-mass spectrometry (MALDI-MS), electrospray ionization-mass spectrometry (ESI-MS), gel permeation-mass spectrometry (GPC-MS)), and fast protein liquid chromatography (FPLC).

In one embodiment, the absence, presence or amount of a structural signature is determined using 1D-NMR or 2D-NMR. The 2D-NMR can be carried out using homonuclear (e.g., COSY, TOCSY, NOESY and ROESY) and/or heteronuclear (e.g., HSQC, HSQC-DEPT, HMQC-COSY, HSQC-TOSCY and HMBC) spectroscopy.

In one embodiment, a sample of unfractionated heparin was reconstituted in water at a concentration of 100 mg/mL. This solution was further diluted and then an appropriate amount of substrate (determined based on the concentration and specific activity of the enzymes involved in the digest) was digested using an enzyme cocktail consisting of *Bacteroides thetaiotaomicron* Heparinase I (600 mIU), *Bacteroides thetaiotaomicron* Heparinase IV (480 mIU), and *Bacteroides thetaiotaomicron* Heparinase III (600 mIU) in 500 mM Bis-tris, 1 M NaCl, pH 7.0. This digestion was performed at 30° C. for 16 hr. In addition, a further digestion of the heparinase-treated sample was performed with the 2-O Sulfatase (1 IU/mg) from *Flavobacterium heparinum* and Δ4,5 glycuronidase (2 IU/mg) for 6 hrs at 30° C.

The resulting solution was passed through 10 kDa MWCO (molecular weight cut-off) filters to remove enzymes and the resulting solution analyzed by ion pairing RPHPLC using tetra-n-butylammonium chloride (TBA) as the ion pair reagent in an acetonitrile (ACN), water, NaCl and Tris buffer at pH 7.0 (Mobile Phase A: 15% ACN, 30 mM TBA, 10 mM Tris; Mobile Phase B: 15% ACN, 30 mM TBA, 10 mM Tris, 1M NaCl). The samples were held at 4° C. during analysis and 45 µL of sample was injected onto the column. The digested sample was separated using a C18 Discovery column (5 µm, 4.6×250 mm) at 25° C. at a flow rate of 0.7 mL/min over 130 min of total run time.

The references, patents and patent applications cited herein are incorporated by reference. Modifications and variations of these methods and products thereof will be obvious to those skilled in the art from the foregoing detailed description and are intended to be encompassed within the scope of the appended claims.

What is claimed:

1. A method of identifying if a process was used to make a heparin preparation, comprising:
performing a separation process on a sample of the heparin preparation determining if a structural signature of one or more of:

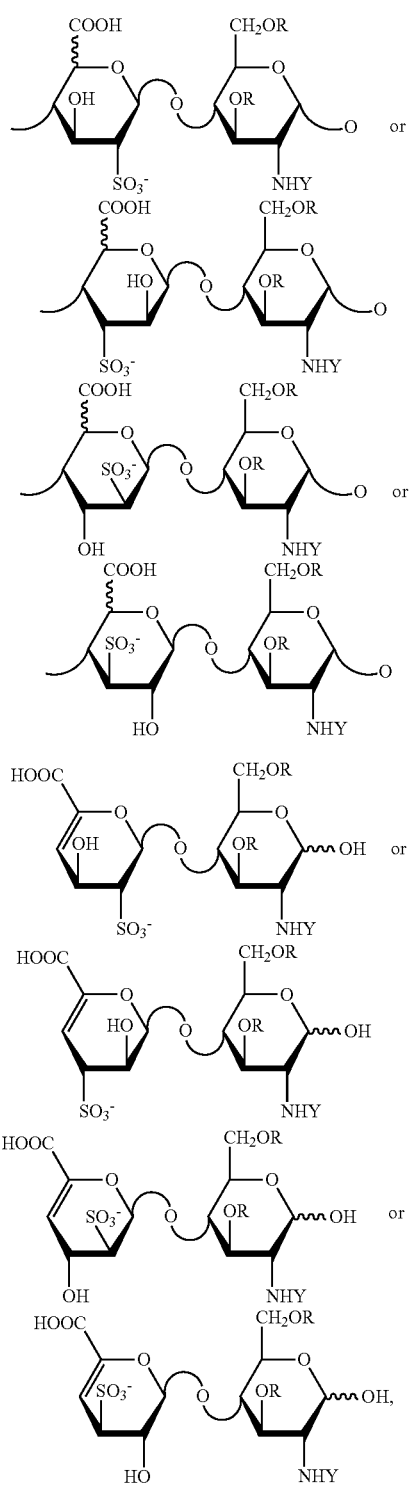

wherein R=SO$_3^-$ or H and Y=SO$_3^-$ or Acetyl, is absent from, present in, or present in an amount in, the separated heparin sample, wherein the presence or amount of the structural signature in the separated heparin sample indicates that the heparin preparation was made by a treatment method that includes treatment with a base, and/or an oxidation process, followed by treatment with a sulfite, and the absence of the structural signature in the separated heparin sample indicates that the heparin preparation was not made by the treatment method; and if the heparin preparation was made by the treatment method, performing a step, wherein the step is one or more of classifying, selecting, accepting, discarding, releasing, withholding, processing into a drug product, shipping, formulating, labeling, packaging, releasing into commerce, selling, and offering for sale the heparin preparation.

2. The method of claim 1, wherein the heparin preparation is an unfractionated heparin preparation or a low molecular weight heparin (LMWH) preparation.

3. The method of claim 1, wherein the heparin preparation is an unfractionated heparin preparation and the step includes further processing the unfractionated heparin preparation to produce a LMWH preparation.

4. The method of claim 1, wherein the heparin preparation is an unfractionated heparin preparation and the processing into drug product includes depolymerizing the unfractionated heparin preparation to produce a LMWH preparation.

5. The method of claim 1, wherein the heparin preparation is a LMWH preparation and the step includes selecting, processing into a drug product, formulating, or labeling the LMWH preparation.

6. The method of claim 1, wherein the method further comprises determining the amount of the structural signature present in the separated heparin sample.

7. The method of claim 1, wherein the separation process performed to determine the absence, presence, or amount of the structural signature is one or more of high performance liquid chromatography (HPLC), nuclear magnetic resonance (NMR), mass spectrometry (MS), capillary electrophoresis (CE), or fast protein liquid chromatography (FPLC).

8. The method of claim 7, wherein the mass spectroscopy (MS) is one or more of gel permeation-mass spectrometry (GPC-MS), matrix-assisted laser desorption ionization-mass spectroscopy (MALDI-MS) or electrospray ionization-mass spectroscopy (ESI-MS).

9. The method of claim 1, wherein the separation process performed to determine the absence, presence, or amount of the structural signature is HPLC.

10. The method of claim 1, wherein the structural signature is a structural signature as peak X of FIG. 1.

11. The method of claim 10, wherein the separation process performed to determine the absence, presence, or amount of the structural signature is high performance liquid chromatography (HPLC), and further one or more of nuclear magnetic resonance (NMR), mass spectrometry (MS), capillary electrophoresis (CE), or fast protein liquid chromatography (FPLC).

12. The method of claim 10, wherein the separation process performed to determine the absence, presence, or amount of the structural signature is HPLC.

13. The method of claim 1, wherein the oxidation process comprises treatment with hydrogen peroxide.

14. The method of claim 1, wherein the sulfite is sodium sulfite.

15. The method of claim 1, wherein the presence of a structural signature of one or more of:

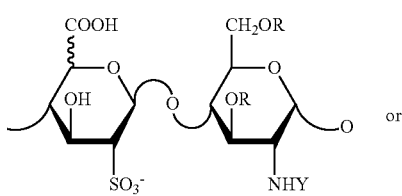

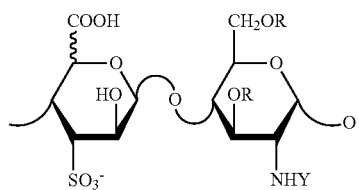

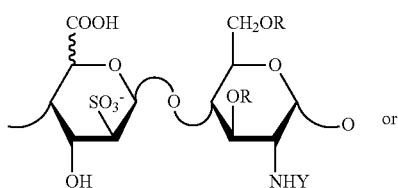

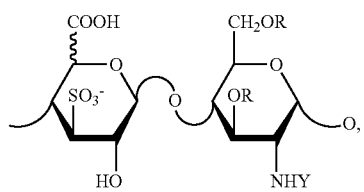

wherein R=SO$_3^-$ or H and Y=SO$_3^-$ or Acetyl, indicates that the heparin preparation was made by the treatment method that includes treatment with a base, and/or an oxidation process, followed by treatment with a sulfite.

16. The method of claim 1, wherein the presence of a structural signature of one or more of:

B

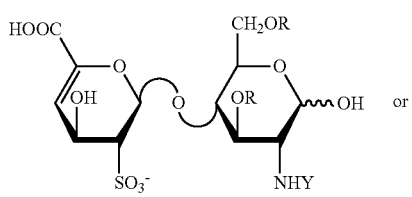

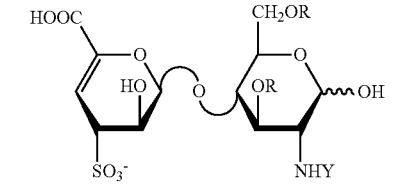

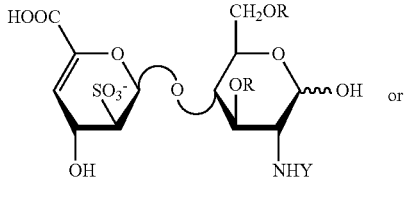

A

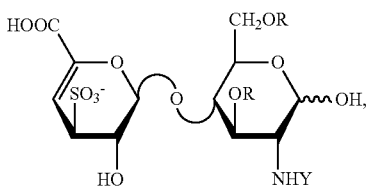

-continued

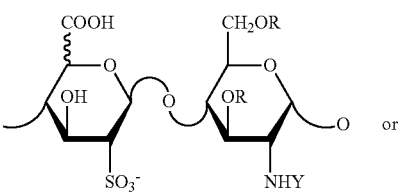 (not applicable)

wherein R=SO$_3^-$ or H and Y=SO$_3^-$ or Acetyl, indicates that the heparin preparation was made by the treatment method that includes treatment with a base, and/or an oxidation process, followed by treatment with a sulfite, further followed by an enzymatic or chemical digestion.

17. The method of claim 16, wherein the digestion comprises an enzymatic digestion with a heparinase.

18. A method of evaluating a heparin preparation, comprising:

identifying if a process was used to make the heparin preparation performing a separation process on a sample of the heparin preparation determining if a structural signature of one or more of:

A

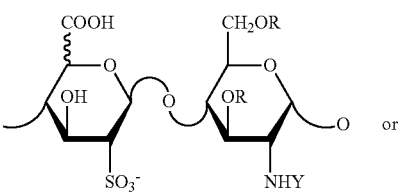

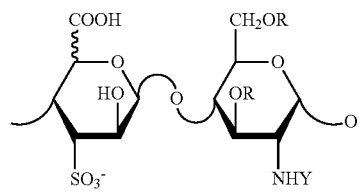

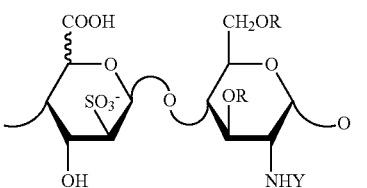

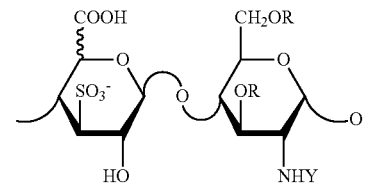

B

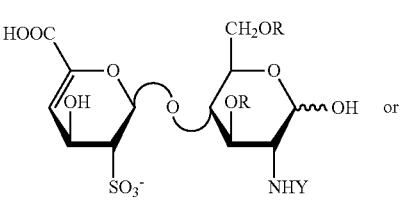

-continued

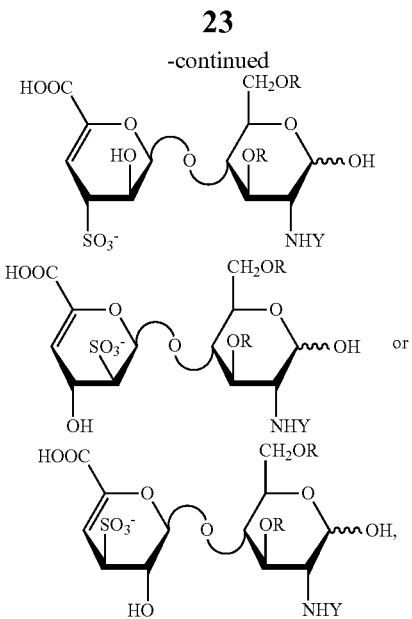

wherein R=SO$_3^-$ or H and Y=SO$_3^-$ or Acetyl, is absent from, present in, or present in an amount in, the separated heparin sample, wherein the presence or amount of the structural signature in the separated heparin sample, indicates that the heparin preparation was made by a treatment method that includes treatment with a base, and/or an oxidation process, followed by treatment with a sulfite, and the absence of the structural signature in the separated heparin sample, indicates that the heparin preparation was not made by the treatment method; and if the heparin preparation was made by the treatment method, performing a step, wherein the step is one or more of classifying, processing into a drug product, formulating, labeling, and packaging the heparin preparation.

19. The method of claim 1, wherein the heparin sample is an unfractionated heparin sample or a low molecular weight heparin (LMWH) sample.

20. A method of producing a LMWH comprising:
providing an unfractionated heparin (UFH) sample from an UFH preparation;
performing a separation process on the UFH sample to determine if a structural signature of one or more of:

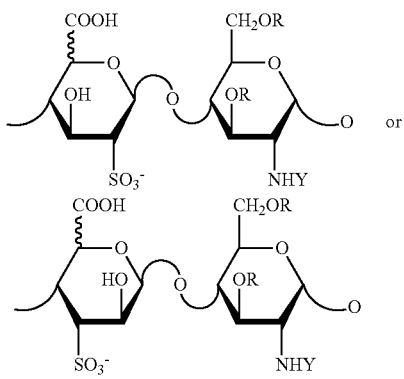

A

-continued

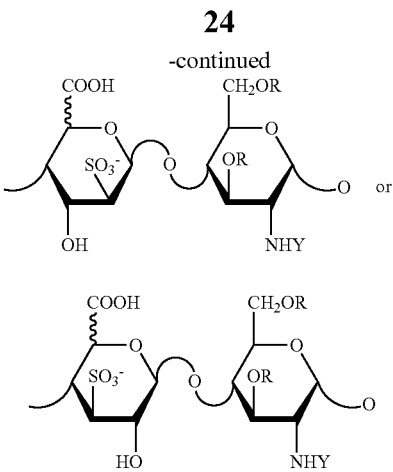

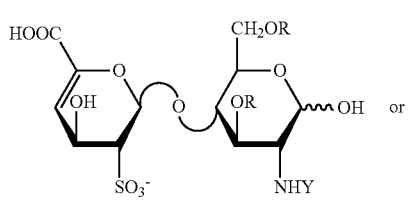

B

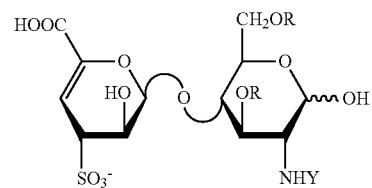

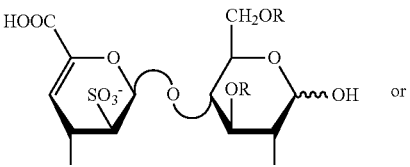

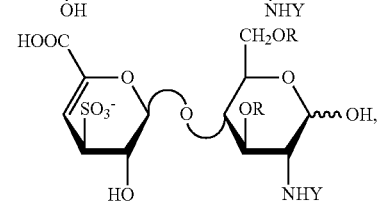

wherein R=SO$_3^-$ or H and Y=SO$_3^-$ or Acetyl, is absent from, present in, or present in an amount in, the separated UFH sample, wherein the presence or amount of the structural signature in the separated UFH sample, indicates that the UFH preparation was made by a treatment method that includes treatment with a base, and/or an oxidation process, followed by treatment with a sulfite, and the absence of the structural signature in the separated UFH sample, indicates that the UFH preparation was not made by the treatment method; and processing the UFH preparation made by the treatment method into a LMWH.

21. A method of producing a LMWH comprising:
performing a separation process on a LMWH sample from a LMWH preparation to determine if a structural signature of one or more of:

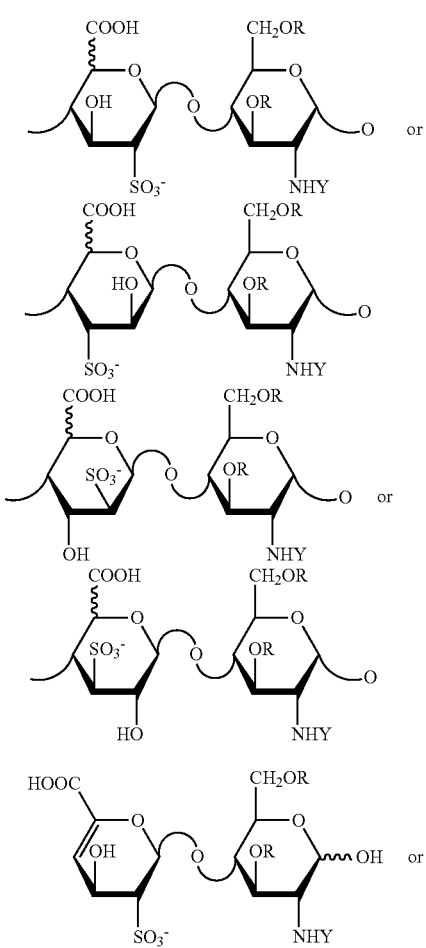
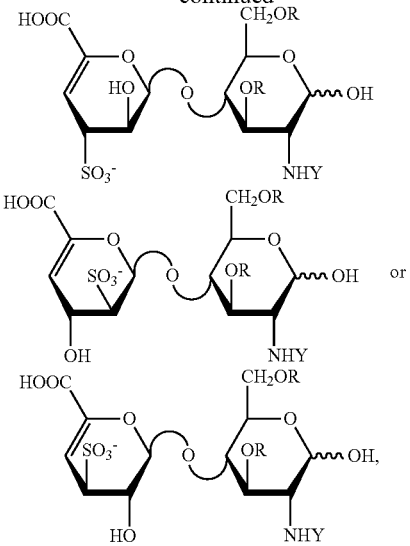

wherein R=$SO_3^-$ or H and Y=$SO_3^-$ or Acetyl, is absent from, present in, or present in an amount in, the separated LMWH sample, wherein the presence or amount of the structural signature in the separated LMWH sample, indicates that the LMWH preparation was made by a treatment method that includes treatment with a base, and/or an oxidation process, followed by treatment with a sulfite, and the absence of the structural signature in the separated LMWH sample, indicates that the LMWH preparation was not made by the treatment method; and processing the LMWH preparation made by the treatment method into a drug product or formulating the LMWH preparation.

* * * * *